(12) United States Patent
Takagi

(10) Patent No.: US 6,768,114 B2
(45) Date of Patent: *Jul. 27, 2004

(54) ELECTRON MICROSCOPE, METHOD FOR OPERATING THE SAME, AND COMPUTER-READABLE MEDIUM

(75) Inventor: Shigenori Takagi, Osaka (JP)

(73) Assignee: Keyence Corporation, Osaka (JP)

( * ) Notice: Subject to any disclaimer, the term of this patent is extended or adjusted under 35 U.S.C. 154(b) by 0 days.

This patent is subject to a terminal disclaimer.

(21) Appl. No.: 10/410,133

(22) Filed: Apr. 10, 2003

(65) Prior Publication Data

US 2003/0193026 A1 Oct. 16, 2003

(30) Foreign Application Priority Data

Apr. 11, 2002 (JP) ..................................... P2002-108931

(51) Int. Cl.[7] .............................................. H01J 37/28
(52) U.S. Cl. ....................... 250/310; 250/311; 250/306; 250/307; 250/397
(58) Field of Search ................................ 250/310, 311, 250/306, 307, 397

(56) References Cited

U.S. PATENT DOCUMENTS 6,531,697 B1 * 3/2003 Nakamura et al. .......... 250/311
6,541,771 B2 * 4/2003 Iwabuchi et al. ........... 250/310

FOREIGN PATENT DOCUMENTS

| JP | 5-62631 | 3/1993 |
| JP | 2001-6588 | 1/2001 |
| JP | 2001-235438 | 8/2001 |
| JP | 2001-338603 | 12/2001 |

* cited by examiner

Primary Examiner—Nikita Wells
(74) Attorney, Agent, or Firm—Morgan, Lewis & Bockius LLP

(57) ABSTRACT

In an electron microscope, at least the characteristics of the specimen is set on a first image observation mode screen as an image observation condition. An observation image of the specimen is displayed on a first display section based on a condition set on the first image observation mode screen. Observation images of the specimen are displayed on a second display section as one or more secondary electron images or one or more reflection electron images under at least two types of image observation conditions based on the condition set on the first image observation mode screen. Any desired observation image is selected from among the observation images displayed on the second display section.

27 Claims, 21 Drawing Sheets

ELECTRON MICROSCOPE, METHOD FOR OPERATING THE SAME, AND COMPUTER-READABLE MEDIUM

BACKGROUND OF THE INVENTION

1. Field of the Invention

This invention relates to an electron microscope such as a scanning electron microscope, a transmission electron microscope, etc., a method for operating the electron microscope, and a computer-readable medium.

2. Description of the Related Art

Nowadays, an electron microscope using an electron lens as well as an optical microscope using an optical lens and a digital microscope is used as an enlargement observation apparatus for enlarging a microbody. The electron microscope is provided by electronically optically designing an image formation system such as an optical microscope as the travel direction of electrons is refracted freely. The available electron microscopes include a transmission electron microscope, a reflection electron microscope, a scanning electron microscope, a surface emission electron microscope (field-ion microscope), and the like. The transmission electron microscope uses an electron lens to form an image of electrons passing through a specimen, a sample, etc. The reflection electron microscope forms an image of electrons reflected on the surface of a specimen. The scanning electron microscope scans a convergent electron beam over the surface of a specimen and uses secondary electrons from the scanning points to form an image. The surface emission electron microscope (field-ion microscope) forms an image of electrons emitted from a specimen by heating or ion application.

The scanning electron microscope (SEM) is an apparatus for using a secondary electron detector, a reflection electron detector, etc., to take out secondary electrons, reflection electrons, etc., occurring upon application of a thin electron beam (electron probe) to an objective specimen and displaying an image on a display screen of a CRT, LCD, etc., for the operator mainly to observe the surface form of the specimen. On the other hand, the transmission electron microscope (TEM) is an apparatus for allowing an electron beam to pass through a thin-film specimen and providing electrons scattered and diffracted by atoms in the specimen at the time as an electron diffraction pattern or a transmission electron-microscopic image, thereby enabling the operator mainly to observe the internal structure of a substance.

When an electron beam is applied to a solid specimen, it passes through the solid by energy of the electrons. At the time, an elastic collision, elastic scattering, and inelastic scattering involving an energy loss are caused by the interaction between the nucleuses and the electrons making up the specimen. As inelastic scattering occurs, the intra-shell electrons of the specimen elements and x-rays, etc., are excited, and secondary electrons are emitted, the energy corresponding thereto is lost. The emission amount of the secondary electrons varies depending on the collision angle. On the other hand, reflection electrons scattered backward by elastic scattering and emitted again from the specimen are emitted in the amount peculiar to the atom number. The scanning electron microscope uses the secondary electrons and the reflection electrons. The scanning electron microscope applies electrons to a specimen and detects the emitted secondary electrons and reflection electrons for forming an observation image.

However, the electron microscope such as SEM or TEM has the disadvantages of a large number of setup items and adjustment items and being difficult to operate as compared with enlargement observation apparatus such as an optical microscope and a digital microscope. Particularly, it is difficult for a beginner unfamiliar with operation of an electron microscope to put the complicated setup items to obtain the best observation image. If an image can be formed, the beginner cannot determine whether or not the image is optimum, and cannot make a fine adjustment to the image, and it is difficult for the beginner even to determine the necessity for the fine adjustment. In some electron microscopes, image observation conditions responsive to the purposes and specimens are preset. However, the beginner cannot recognize the significance of setting the image observation condition based on the characteristics of the electric conductivity, etc., of the specimen, and cannot determine which to select either. Thus, only skilled expert operators would be able to operate electron microscopes. Particularly, an image formed under the setup condition cannot immediately be acquired and thus the operator cannot determine the setup condition while checking the screen, resulting in difficulty in operating the electron microscope.

A general optical microscope involves main adjustment items of specimen positioning, magnification, focus, and brightness, and if the adjustment items are determined, an observation image can be acquired. If each adjustment item is changed, an observation image on which the adjustment item change result is reflected can be provided immediately, so that the operator can change the setting while visually checking the adjustment effect. In contrast, the electron microscope involves various setup and adjustment items and in addition, it is hard to predict what observation image is provided as a result of changing the items, and the operator must check the actually provided image on the screen. In addition, if the setting is changed, it takes time until an image on which the setting change is reflected is provided, and thus the operator cannot check the adjustment effect in real time. For example, with the SEM, while a signal from an arbitrary point on the specimen to be observed is detected, the whole area is scanned and further image processing of the detected signal is performed, thereby forming an image. Thus, it takes time of several ten seconds until one observation image is provided. Therefore, if setting is changed, the above-described operation needs to be again performed from the beginning to acquire an observation image; the operator must wait until an observation image is provided. Thus, the operator cannot promptly check the effect of the setting and it becomes hard for the operator to grasp the effect of setting adjustment on the observation image, resulting in difficulty in operating the electron microscope.

Further, if the acceleration voltage is raised excessively, charge-up occurs and it is made impossible to acquire a normal observation image. In addition, once charge-up occurs, labor to eliminate the charge-up is required; this is also a problem. The problem of charge-up is one factor in making it difficult to operate the electron microscope. Since the electron microscope involves the problems as described above, after all, the operation of the electron microscope depends largely on the experience of the operator, and an electron microscope that can be easily operated by a beginner is expected.

SUMMARY OF THE INVENTION

It is therefore an object of the invention to provide an electron microscope provided with a guidance function to facilitate setting the electron microscope, a method for operating n electron microscope, and a computer-readable medium.

In order to accomplish the object above, the following means are adopted. According to a first aspect of the present invention, there is provided an electron microscope for picking up an observation image of a specimen based on an image observation condition, the electron microscope comprising:

a first setting section for setting at least characteristics of the specimen as an image observation condition on a first image observation mode screen;

a first display section for displaying an observation image of the specimen based on the condition set through the first setting section;

a second display section for displaying at least one observation image of the specimen including at least one secondary electron image or at least one reflection electron image under at least two types of image observation conditions based on the condition set through the first setting section; and a selection section for selecting a desired observation image from among the observation images displayed on the second display section.

The electron microscope according to a second aspect of the present invention is characterized by the fact the second display section displays a plurality of observation images of the specimen including a plurality of secondary electron images in addition to the characteristic according to the first aspect of the present invention.

The electron microscope according to a third aspect of the present invention is characterized by the fact that the second display section displays a plurality o observation images of the specimen including a plurality of reflection electron images in addition to the characteristic according to the first aspect of the present invention.

The electron microscope according to a fourth aspect of the present invention is characterized by the fact that the second display section displays a plurality of the observation images of the specimen including at least one secondary electron image and at least one reflection electron image in addition to the characteristic according to the first aspect of the present invention.

The electron microscope according to a fifth aspect of the present invention is characterized by the fact that it further comprises:

a second setting section for setting at least a spot size of an electron beam on the specimen, an acceleration voltage, a detector type, a specimen position, and an observation magnification as image observation conditions on a second image observation mode screen; and a mode switch section for switching the first image observation mode screen and the second image observation mode screen, in addition to the characteristic according to the first aspect of the present invention.

The electron microscope according to a sixth aspect of the present invention is characterized by the fact that the at least two types of image observation conditions include at least two types of acceleration voltages or spot sizes changed, in addition to the characteristic according to the first aspect of the present invention.

The electron microscope according to a seventh aspect of the present invention is characterized by the fact that it further comprises:

an observation positioning section for moving the observation image displayed on the first display section to a predetermined position on the first display section; and an observation magnification change section for changing an observation magnification of the observation image displayed on the first display section, wherein the second display section displays the at least one observation images of the specimen at the observation position and the observation magnification set through the observation positioning section and the observation magnification change section, in addition to the characteristic according to the first aspect of the present invention.

The predetermined position can be roughly the center of the first display section, for example. The characteristics of the specimen can also be determined based on the electric conductivity of the specimen to be observed.

The electron microscope according to a eighth aspect of the present invention is characterized by the fact that it further comprising:

an adjustment section for adjusting at least any of focus, contrast, or brightness with respect to the observation image selected through the selection section in the first image observation mode, in addition to the characteristic according to the first aspect of the present invention.

The electron microscope according to a ninth aspect of the present invention is characterized by the fact that the at least one secondary electron image includes a secondary electron image acquired with an acceleration voltage set to 5 kV or less and a secondary electron image acquired with an acceleration voltage set to 10 kV or more, in addition to the characteristic according to the first aspect of the present invention.

The electron microscope according to a tenth aspect of the present invention is characterized by the fact that the at least one reflection electron image includes a reflection electron image acquired with an acceleration voltage set to 10 kV or more, in addition to the characteristic according to the first aspect of the present invention.

The electron microscope according to an eleventh aspect of the present invention is characterized by the fact that the acceleration voltage set for each of the secondary electron images or the reflection electron images displayed on the second display section is determined according to a predetermined procedure, in addition to the characteristic according to the first aspect of the present invention.

The electron microscope according to a twelfth aspect of the present invention is characterized by the fact that the second setting section sets an astigmatism to a predetermined value on the second image observation mode screen, in addition to the characteristic according to the fifth aspect of the present invention.

The electron microscope according to a thirteenth aspect of the present invention is characterized by the fact that the second setting section sets an optical axis adjustment on the second image observation mode screen based on a correlation table prepared based on at least the relationship between the acceleration voltage and the spot size, in addition to the characteristic according to the fifth aspect of the present invention.

The electron microscope according to a fourteenth aspect of the present invention is characterized by the fact that it further comprises:

an automatic adjustment section for automatically adjusting an observation magnification of the observation image displayed on the first display section or the second display section to a magnification for enabling the whole of the specimen to be displayed, in addition to the characteristic according to the first aspect of the present invention.

Further, in order to accomplish the object above, according to a fifteenth aspect of the present invention, there is provided an electron microscope comprising:

an electron gun for applying an electron beam;

a gun alignment coil for making a correction to the electron beam applied from the electron gun so that the electron beam passes through the center of a lens system;

a converging lens for narrowing down a size of a spot of the electron beam;

an electron beam deflection scanning coil for scanning the electron beam converged through the converging lens over a specimen;

a detector for detecting secondary electrons or reflection electrons output from the specimen with scanning;

a display section for displaying an observation image based on the secondary electrons or the reflection electrons; and a guidance section for guiding an operator through a setting procedure of a setup item required for setting at least an acceleration voltage or spot size as an image observation condition.

The electron microscope according to a sixteenth aspect of the present invention is characterized by the fact that the guidance section prompts the operator to select or enter a setup item to be set in an interactive mode and determines a necessary setup item based on the setting by the operator, in addition to the characteristic according to the fifteenth aspect of the present invention.

The electron microscope according to a seventeenth aspect of the present invention is characterized by the fact that the guidance section comprises an explanation display section for explaining selection or entry of a setup item to be set and for displaying an explanation about the setup item to be set, in addition to the characteristic according to the fifteenth aspect of the present invention.

The explanation display section can explain the setup item in text, an image, or voice or a combination thereof.

The electron microscope according to a eighteenth aspect of the present invention is characterized by the fact that the guidance section comprises:

a first setting section for selecting at least characteristics of the specimen as an image observation condition; and an observation magnification change section for changing an observation magnification of an observation image of the specimen displayed on the display section based on the condition set through the first setting section, in addition to the characteristic according to the fifteenth aspect of the present invention.

The electron microscope according to a nineteenth aspect of the present invention is characterized by the fact that the display section comprises:

a first display section for displaying the observation image of the specimen based on the condition set through the first setting section; and a second display section for displaying at least one observation image of the specimen including at least one secondary electron image or at least one reflection electron image under at least the acceleration voltage or the spot size changed at the observation magnification set through the observation magnification change section, in addition to the characteristic according to the eighteenth aspect of the present invention.

The electron microscope according to a twentieth aspect of the present invention is characterized by the fact that the guidance section comprises;

an observation positioning section for moving the observation image displayed on the first display section to a predetermined position on the first display section, in addition to the characteristic according to the nineteenth aspect of the present invention.

Further, in order to accomplish the object above, according to a twenty-first aspect of the present invention, there is provided a method for operating an electron microscope for picking up an observation image of a specimen based on an image observation condition, the method comprising:

setting at least characteristics of the specimen as an image observation condition on a first image observation mode screen;

displaying an observation image of the specimen on a first display section based on the condition set through the setting step;

displaying at least one observation image of the specimen including at least one secondary electron image or at least one reflection electron image under at least two types of image observation conditions based on the condition set through the setting step; and selecting a desired observation image from among the observation images displayed on the second display section.

The electron microscope may further comprises:

moving the observation image displayed on the first display section to a predetermined position on the first display section; and determining an observation magnification of the observation image displayed on the first display section, wherein the at least one observation image of the specimen is displayed on the second display section at the determined observation position and observation magnification.

Further, it may further comprises:

moving the observation image displayed on the first display section to a predetermined position on the first display section; and adjusting the observation magnification of the observation image displayed on the first display section, wherein the at least one observation image of the specimen is displayed on the second display section at the adjusted observation magnification.

The electron microscope according to a twenty-second aspect of the present invention is characterized by the fact that it further comprises:

selecting either the first image observation mode screen or a second image observation mode screen as a screen for setting an image observation condition; and setting at least a spot size of an electron beam on the specimen, an acceleration voltage, a detector type, a specimen position, and an observation magnification when the second image observation mode screen is selected, in addition to the characteristic according to the twenty-first aspect of the present invention.

The electron microscope according to a twenty-third aspect of the present invention is characterized by the fact that the at least two types of image observation conditions include at least two types of acceleration voltage or spot size changed, in addition to the characteristic according to the twenty-first aspect of the present invention.

The electron microscope according to a twenty-fourth aspect of the present invention is characterized by the fact that it further comprises:

selectively adjusting at least any of focus, contrast, or brightness with respect to the selected desired observation image, in addition to the characteristic according to the twenty-first aspect of the present invention.

The electron microscope according to a twenty-fifth aspect of the present invention is characterized by the fact that the moving step or the magnification adjusting step is automatically conducted based on a preset default value, in addition to the characteristic according to the twenty-first aspect of the present invention.

The electron microscope according to a twenty-sixth aspect of the present invention is characterized by the fact that the moving step moves a specimen table on which the specimen is placed, in addition to the characteristic according to the twenty-first aspect of the present invention.

The electron microscope according to a twenty-seventh aspect of the present invention is characterized by the fact that the moving step shifts a scan position of an electron beam applied from the electron gun, in addition to the characteristic according to the twenty-first aspect of the present invention.

The electron microscope according to a twenty-eight aspect of the present invention is characterized by the fact that it further comprises:

warning an operator that entry contents are erroneous, in addition to the characteristic according to the twenty-first aspect of the present invention.

The electron microscope according to a twenty-ninth aspect of the present invention is characterized by the fact that it further comprises:

setting a predetermined setup item as a limitation item which is inhibited from being set in each step, in addition to the characteristic according to the twenty-first aspect of the present invention.

The electron microscope according to a thirtieth aspect of the present invention is characterized by the fact that it further comprises:

setting a predetermined setup item which need not be set as nondisplay setup item in each step, in addition to the characteristic according to the twenty-first aspect of the present invention.

The electron microscope according to a thirty-first aspect of the present invention is characterized by the fact that the observation image displayed on the first display section is automatically moves roughly to the center on the first display section based on a preset default value, and the observation magnification of the observation image displayed on the first display section is automatically adjusted based on a preset default value, and wherein the at least one observation image of the specimen is displayed on the second display section at the adjusted observation magnification, in addition to the characteristic according to the twenty-first aspect of the present invention.

Further, according to a thirty-second aspect of the present invention, there is provided a computer-readable medium including a program executable on a computer for operating an electron microscope which picks up an observation image of a specimen based on an image observation condition, the program comprising instructions having:

a first function of selecting at least characteristics of the specimen as an image observation condition on a first image observation mode screen;

a second function of displaying an observation image of the specimen on a first display section based on the condition set through the first function;

a third function of moving the observation image displayed on the first display section to a predetermined position on the first display section;

a fourth function of changing an observation magnification of the observation image displayed on the first display section;

a fifth function of displaying at least one observation image of the specimen including at least one secondary electron image or at least one reflection electron image on a second display section under at least two types of image observation conditions at the observation position and the observation magnification set through the third and fourth functions; and a sixth function of selecting a desired observation image from among the observation images displayed on the second display section.

The electron microscope according to a thirty-third aspect of the present invention is characterized by the fact that it further comprises:

a seventh function of switching a screen for setting an image observation condition between a second image observation mode screen and the first image observation mode screen; and a eighth function of setting at least a spot size of an electron beam on the specimen, an acceleration voltage, a detector type, a specimen position, and an observation magnification on the second image observation mode screen, in addition to the characteristic according to the thirty-third aspect of the present invention.

The medium includes a magnetic disk, an optical disk, a magneto-optical disk, semiconductor memory, or any other medium capable of storing a program, such as CD-ROM, CD-R, CD-RW, flexible disk, magnetic tape, MO, DVD-ROM, DVD-RAM, DVD-R, DVD-RW, OR DVD+RW.

To observe under an electron microscope such as a SEM, steps indispensable for operation, such as searching for a visual field and condition setting, exist. The invention focuses attention on this point; necessary steps are explained for each screen and the operator is guided stepwise in operating the electron microscope for simplifying the operation of the electron microscope. To guide the operator in operating the electron microscope, flow form or wizard form can be used. A plurality of screens are provided in response to the setup item and are switched in order for display, whereby the operator is requested to enter condition required for image observation in a general way. Explanation is displayed for each screen and the item which needs to be specified on the screen is explained for the operator and the operator is also prompted to enter or select. Based on the entered information, each setup value is computed or the default value is entered as required for automatically setting necessary items. The operable range or items can also be limited for each screen for preventing erroneous entry or malfunction. In addition to the auto observation mode thus guiding the operator through the operation procedure, a manual observation mode for the operator to set all setup items is also provided and the operator can switch the auto and manual observation modes as he or she desires.

DETAILED DESCRIPTION OF THE INVENTION

Figure 1:
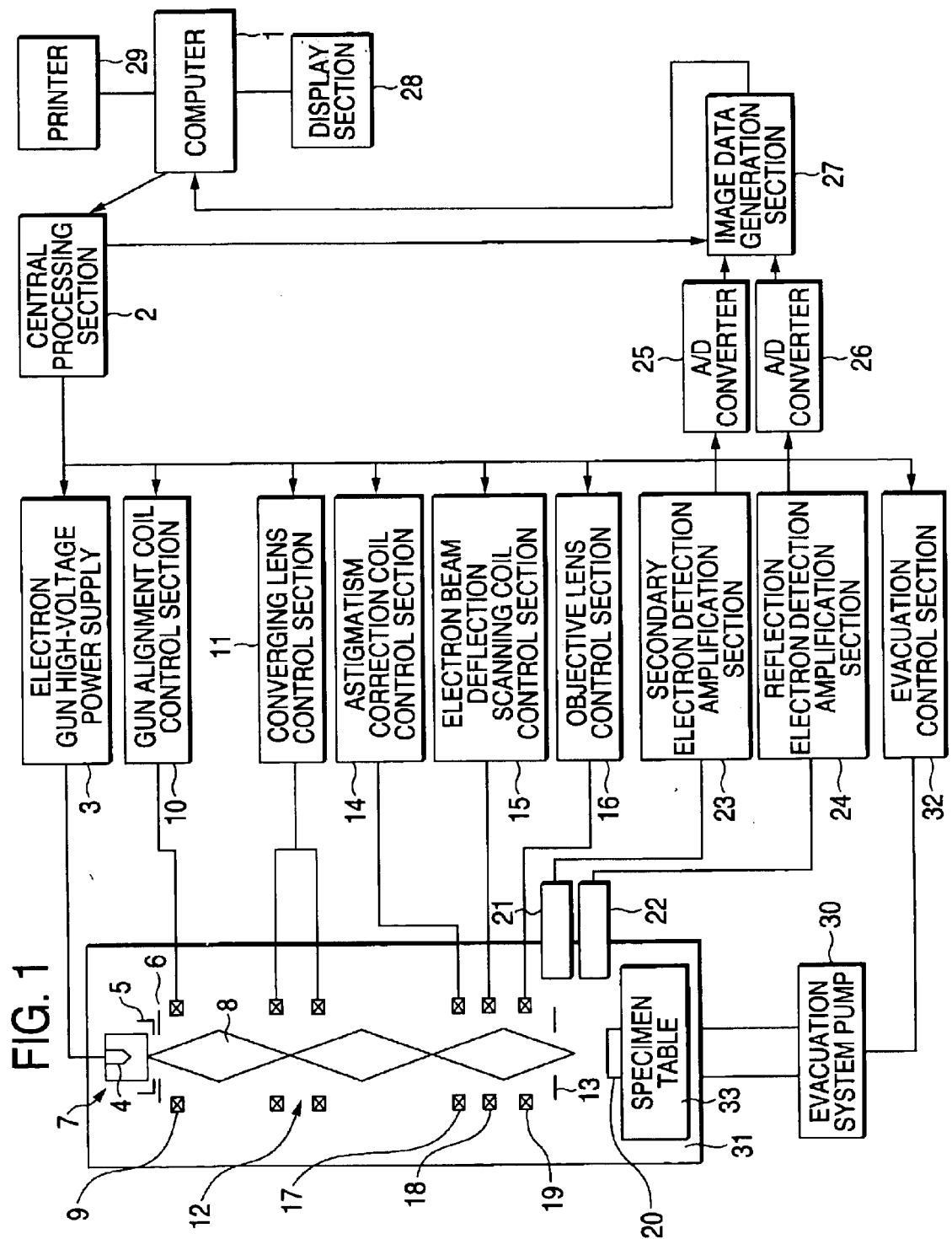
FIG. 1 is a block diagram to show the configuration of a scanning electron microscope according to one embodiment of the invention.

Referring now to the accompanying drawings, there is shown a preferred embodiment of the invention. However, it is to be understood that the following embodiment is illustrative for an electron microscope, an electron microscope operation method, an electron microscope operation program, and a computer-readable medium to embody the technical philosophy of the invention and that the invention does not limit the electron microscope, the electron microscope operation method, the electron microscope operation program, and the computer-readable medium to the following.

It is also to be understood that the specification does not limit the members defined in the appended claims to the members in the embodiment. The sizes of members shown in the accompanying drawings, their positional relationship, and the like may be exaggerated to clarify the description.

In the specification, an electron microscope, a computer, and other peripheral machines of a printer, etc., are electrically connected, for example, as serial connection or parallel connection of IEEE1394, RS-232C, RS-422, USB, etc., or through a network of 10BASE-T, 100BASE-TX, etc., for conducting communications. The connection is not limited to physical connection using wires and may be wireless connection using radio waves, infrared rays, optical communications, etc., such as wireless LAN, Bluetooth, etc. Further, a memory card, a magnetic disk, an optical disk, a magneto-optical disk, semiconductor memory, etc., can be used as a record medium for storing data of observation images, etc.

In the embodiment, an example wherein an electron microscope operation program is installed in a computer 1 in FIG. 1 for use will be discussed. As image data, an analog signal is converted into a digital signal, which is then processed. As for the image data of a digital signal, degradation of the image does not occur and image change, image integration, pseudo-coloring, and the like are easy to perform. However, the analog signal need not necessarily be converted into a digital signal, and an image of an analog signal can also be handled.

"Computer" mentioned in the specification is not limited to the computer to which an electron microscope is connected. For example, an electron microscope operation program of the invention can also be used in the form wherein for the operator to learn an operation method of the electron microscope, the electron microscope operation program is installed in a computer not connected to the electron microscope for operation. The computer includes not only a general-purpose or special-purpose computer, workstation, terminal, or any other electronic device in which the electron microscope operation program is installed, but also hardware such as a dedicated apparatus in which an electron microscope operation function is built or an electron microscope itself. The program includes every form for providing a specific function as software of a plug-in, an object, a library, an applet, a compiler, etc.

The following operation is performed through a mouse, a trackball, a track point, a lightpen, a digitizer, or any other input means connected to a computer or electron microscope. Various operation buttons and controls installed on a console of an electron microscope can also be used to operate and set the electron microscope.

The phrase "pressing a button" in the specification is used to mean that if the button is formed virtually on the monitor screen of a computer, the operator clicks on the button with an input device such as a mouse, thereby pressing the button in a pseudo manner. However, not only the method, but also various mechanisms can be used in response to the operation screen. For example, if the operator console is formed on a touch screen or a touch panel, the operator can directly touch the operation console for operation. Alternatively, the operator can also use a lightpen, etc., to specify operation or if the operator console is implemented as a physical operator control panel, the operator operates it physically.

In the following embodiment, a SEM will be discussed. However, the invention can also be used with a TEM or any other electron microscope relevant apparatus. The SEM according to one embodiment of the invention will be discussed with reference to FIG. 1. The SEM generally is made up of an optical system for generating an electron beam of acceleration electrons and making the electron beam arrive at a specimen, a specimen chamber in which a specimen is placed, an evacuation system for evacuating the specimen chamber, and an operation system for observing an image.

The optical system comprises an electron gun 7 for generating an electron beam of acceleration electrons, a lens system for narrowing down a bundle of acceleration electrons to a narrower bundle, and detectors for detecting secondary electrons and reflection electrons generated from a specimen. The scanning electron microscope shown in FIG. 1 has an optical system comprising an electron gun 7, a gun alignment coil 9, condenser lenses of converging lenses 12, an electron beam deflection scanning coil 18, a secondary electron detector 21, and a reflection electron detector 22. The electron gun 7 applies an electron beam. The gun alignment coil 9 makes a correction to the electron beam applied from the electron gun 7 so that the electron beam passes through the center of a lens system. The condenser lenses of converging lenses 12 narrows down the size of the spot of the electron beam. The electron beam deflection scanning coil 18 scans the electron beam converged through the converging lenses 12 over a specimen 20. The secondary electron detector 21 detects secondary electrons emitted from the specimen 20 with scanning. The reflection electron detector 22 detects reflection electrons.

The specimen chamber comprises a specimen table, a specimen introduction unit, an X-ray detection spectroscope, etc. The specimen table comprises X, Y, Z move, rotation, and tilt functions.

The evacuation system is required for the electron beam of acceleration electrons to arrive at the specimen without losing energy as much as possible while the electron beam passes through the gas component; it mainly uses a rotary pump, an oil diffusion pump.

The operation system adjusts, focuses, etc., an application current while displaying a secondary electron image, a reflection electron image, an X-ray image, etc., for observation. Output of a secondary electron image, etc., is typically film photographing with a camera if the signal is analog; in recent years, however, it has been made possible to convert an image into a digital signal for output, and various types of processing such as data storage, image processing, and print are possible. The SEM in FIG. 1 comprises a display section 28 for displaying an observation image of a secondary electron image, a reflection electron image, etc., and a printer 29 for printing the image. The operation system comprises a guide section for guiding the operator through a setting procedure of a setup item required for setting at least acceleration voltage or spot size as an image observation condition.

The SEM shown in FIG. 1 is connected to a computer 1 for use as a console for operating the electron microscope; the computer 1 also stores image observation conditions and image data and performs image processing and operations as required. A central processing section 2 made up of a CPU, LSI, etc., shown in FIG. 1 controls the blocks making up the electron microscope. An electron gun high-voltage power supply 3 is controlled, whereby an electron beam is generated from the electron gun 7 consisting of a filament 4, Wehnelt 5, and an anode 6. An electron beam 8 generated from the electron gun 7 does not necessarily pass through the center of the lens system and a gun alignment coil control section 10 controls the gun alignment coil 9 for making a correction to the electron beam so that the electron beam passes through the center of the lens system. Next, the electron beam 8 is narrowed down through the condenser lenses of the converging lenses 12 controlled by a converging lens control section 11. The converged electron beam 8 passes through an astigmatism correction coil 17 for deflecting the electron beam 8, the electron beam deflection scanning coil 18, an objective lens 19, and objective lens stop 13 for determining the beam aperture angle of the electron beam 8, and arrives at the specimen 20. The astigmatism correction coil 17 is controlled by an astigmatism correction coil control section 14, and controls scanning speed, etc. Likewise, the electron beam deflection scanning coil 18 is controlled by the electron beam deflection scanning coil control section 15, and the objective lens 19 is controlled by an objective lens control section 16, whereby the electron beam 8 scans over the specimen 20. As the electron beam 8 scans over the specimen 20, information signals of secondary electrons, reflection electrons, etc., are generated from the specimen 20, and are detected by the secondary electron detector 21 and the reflection electron detector 22. The detected secondary electron information signal and the detected reflection electron information signal are passed through a secondary electron detection amplification section 23 and a reflection electron detection amplification section 24 and are converted into digital signals by A/D converters 25 and 26 respectively. The digital signals are sent to an image data generation section 27 for providing image data. The image data is sent to the computer 1 and is displayed on the display section 28 such as a monitor connected to the computer 1 and is printed on the printer 29 as required.

An evacuation system pump 30 evacuates a specimen chamber 31. An evacuation control section 32 connected to the evacuation system pump 30 adjusts the vacuum degree for controlling the vacuum degree from high vacuum to low vacuum in response to the specimen 20 and the observation purpose.

The electron gun 7 is a section as a source for generating an acceleration electron having one energy; in addition to a heat electron gun for heating a W (tungsten) filament or an $LaB_6$ filament to emit electrons, a field emission electron gun for applying a strong electric field to the tip of W formed like a point for emitting electrons is available. Converting lens, objective lens, objective lens stop, electron beam deflection scanning coil, astigmatism correction coil, and the like are placed in the lens system. The converging lens further converges the electron beam generated by the electron gun and thins down the electron beam. The objective lens is a lens for finally focusing an electron probe on a specimen. The objective lens stop is used to lessen aberration. The detectors are a secondary electron detector for detecting secondary electrons and a reflection electron detector for detecting reflection electrons. The secondary electron has low energy and thus is captured by a collector and is converted into a photoelectron by a scintillator and the signal is amplified by a photomultiplier tube. On the other hand, to detect a reflection electron, a scintillator or a semiconductor type is used.

[Specimen Table]

To position the observation position, a specimen table 33 on which a specimen 20 is placed is moved physically. In this case, an observation positioning section is implemented as the specimen table 33. The specimen table 33 can be moved and adjusted in various directions so that the observation position of the specimen 20 can be adjusted. To move and adjust the observation position of the specimen table, the specimen table can be moved and finely adjusted in an X axis direction, a Y axis direction, and an R axis direction of the specimen table. In addition, to adjust the tilt angle of the specimen, the specimen table can be adjusted in a T axis direction of the specimen table and to adjust the distance between the objective lens and the specimen (working distance), the specimen table can be adjusted in a Z axis direction of the specimen table.

[Mode]

Figure 2:
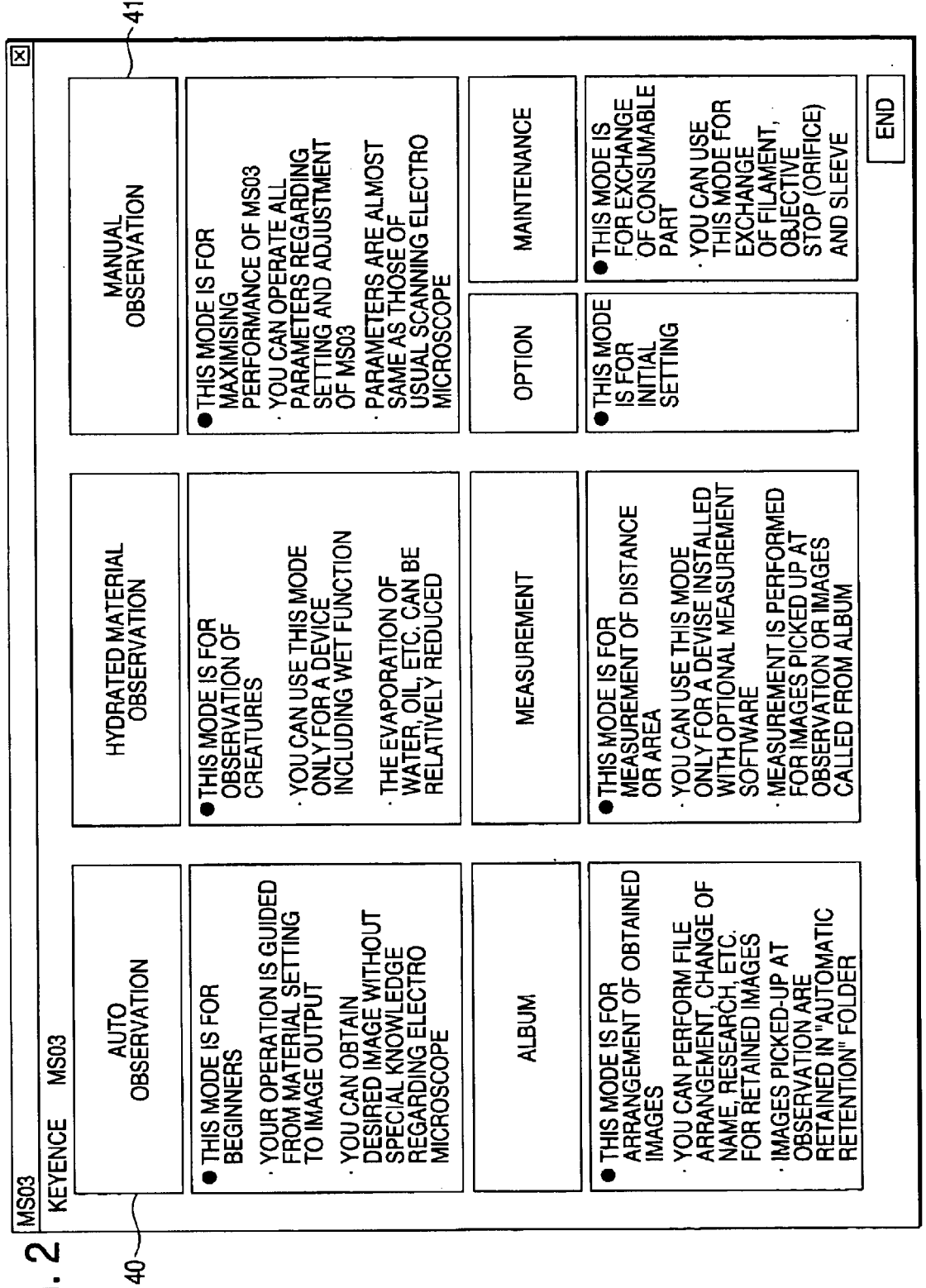
FIG. 2 is an image drawing to show a menu screen of a scanning electron microscope operation program according to one embodiment of the invention.
Figure 3:
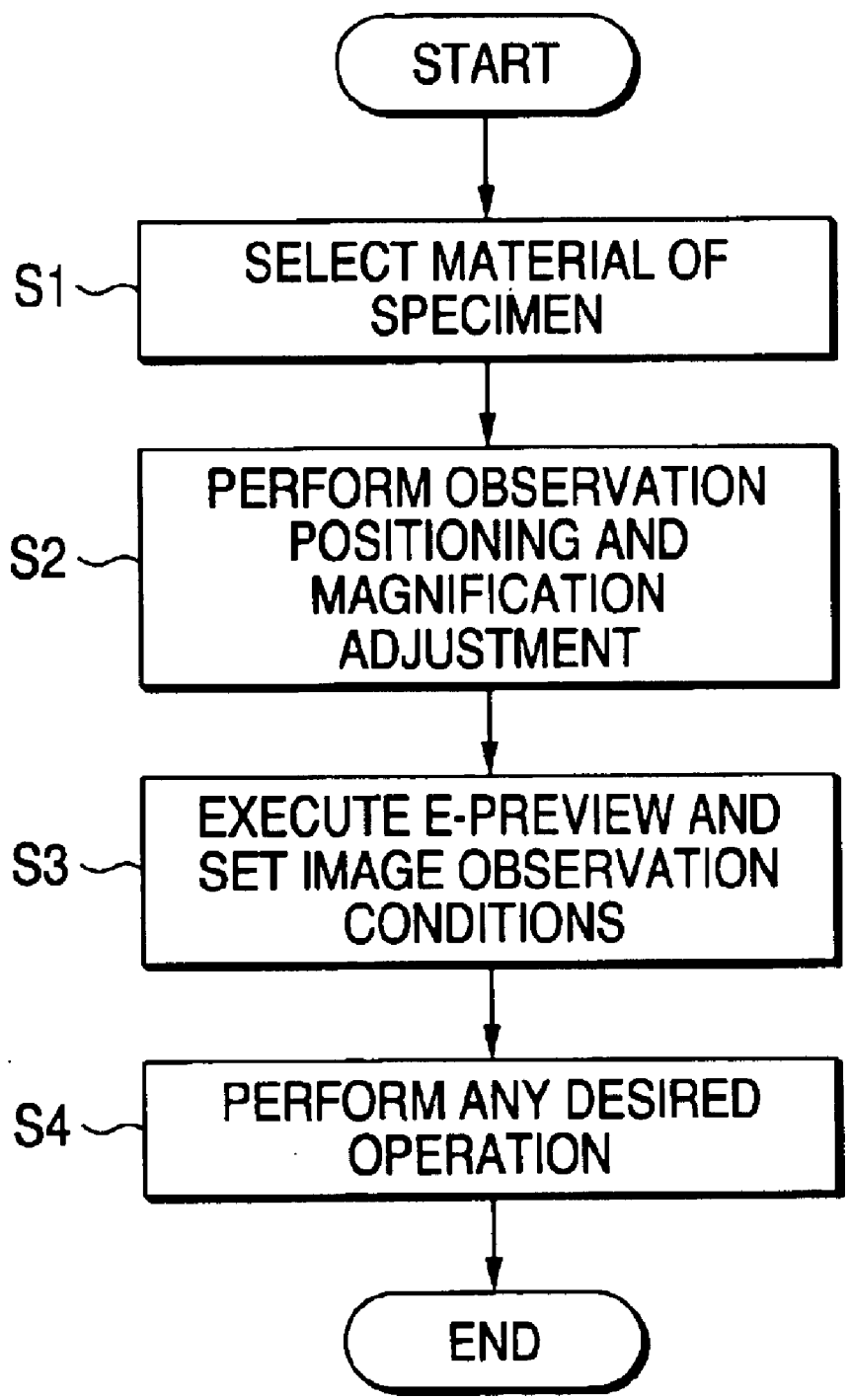
FIG. 3 is a flowchart to show steps of image observation according to an auto observation mode of an electron microscope operation method according to one embodiment of the invention.
Figure 4:
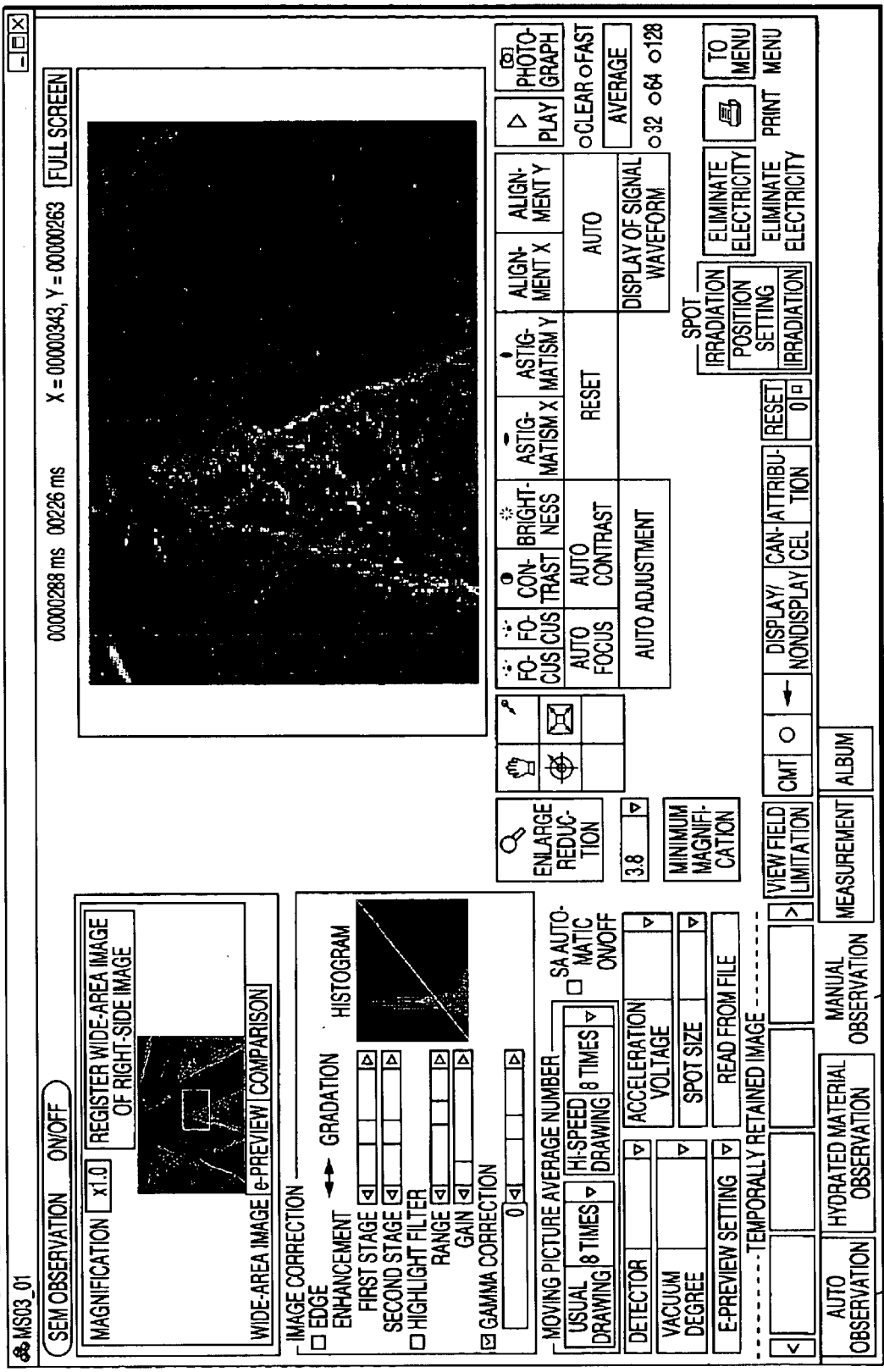
FIG. 4 is an image drawing to show a manual observation mode of the scanning electron microscope operation program according to the embodiment of the invention.

The electron microscope comprises a first image observation mode screen provided with a guidance function of guiding the operator in setting to facilitate operation of the electron microscope and a second image observation mode screen for enabling the operator to set the electron microscope in a conventional manner. The first image observation mode screen provides an easy mode for guiding the operator in setting of necessary items to make it possible to automatically set the electron microscope to some extent so that a reasonable observation image can be acquired even if the operator is unfamiliar with operation of the electron microscope. The first image observation mode is represented as AUTO OBSERVATION 40 on a menu screen of an electron microscope operation program shown in FIG. 2. FIGS. 2 and 4 and later show images of user interface screens of the electron microscope operation program.

On the other hand, the second image observation mode screen is a usual setting screen and provides a professional mode for a person skilled in operation of the electron microscope to set the electron microscope in detail to acquire an optimum observation image. The second image observation mode is represented as MANUAL OBSERVATION 41 in FIG. 2. FIG. 4 shows a screen example of the manual observation mode. In the manual observation mode, the operator sets all setup items. The screen does not guide the operator in setting and enables the operator to perform every possible type of operation at all times so that the operator can determine the operation at any timing.

[Image Observation Condition]

The image observation condition required for providing an observation image under the SEM is to determine an appropriate acceleration voltage value in response to a specimen as the electron gun high-voltage power supply 3, etc., is adjusted in acceleration voltage, to set the electron beam applied from the electron gun to any desired spot size (diameter of incident electron beam bundle), etc., for example. Any other image observation condition than the acceleration voltage or the spot size includes selection of any of secondary electron detector, reflection electron detector, etc., as a detector, the vacuum degree in the specimen chamber 31, the magnification, the observation position of a specimen, namely, the X, Y, R axis position of the specimen table, the tilt angle of a specimen, namely, the T axis position of the specimen table, the working distance, namely, the Z axis position of the specimen table, the objective stop diameter, etc.

The adjustment items are items which need to be adjusted only once and items which need to be adjusted each time the image observation condition is changed. For example, the current value for heating the filament to generate heat electrons from the electron gun needs to be adjusted only once at the operation starting time of the electron microscope. In contrast, adjustment items of an acquired observation image include focus, contrast, brightness, astigmatism correction, optical axis adjustment (gun alignment), etc. The operator sets the items by operating necessary buttons and menus on the screen.

The operator of the electron microscope can switch the observation mode between the auto observation mode and the manual observation mode by selecting an AUTO OBSERVATION tab 42 or a MANUAL OBSERVATION tab 43 provided at the bottom in FIG. 4. The operator can switch the observation mode from the manual observation mode to the auto observation mode or from the auto observation mode to the manual observation mode at any time. Accordingly, it is made possible to acquire a reasonable observation image in the auto observation mode and then switch into the manual observation mode to adjust to optimum setting for providing a more detailed observation image, for example, as a use mode.

[Electron Microscope Operation Method of in Auto Observation Mode]

As an electron microscope operation method according to one embodiment of the invention, image observation in the auto observation mode will be discussed with reference to operation screens in FIGS. 6 to 15 and 24 to 26. Each drawing shows an example of the user interface screen displayed on the computer or the electron microscope. The design and layout of each screen, button layout, color arrangement, icon shapes, and the like can be changed whenever necessary, needless to say.

Figure 5:
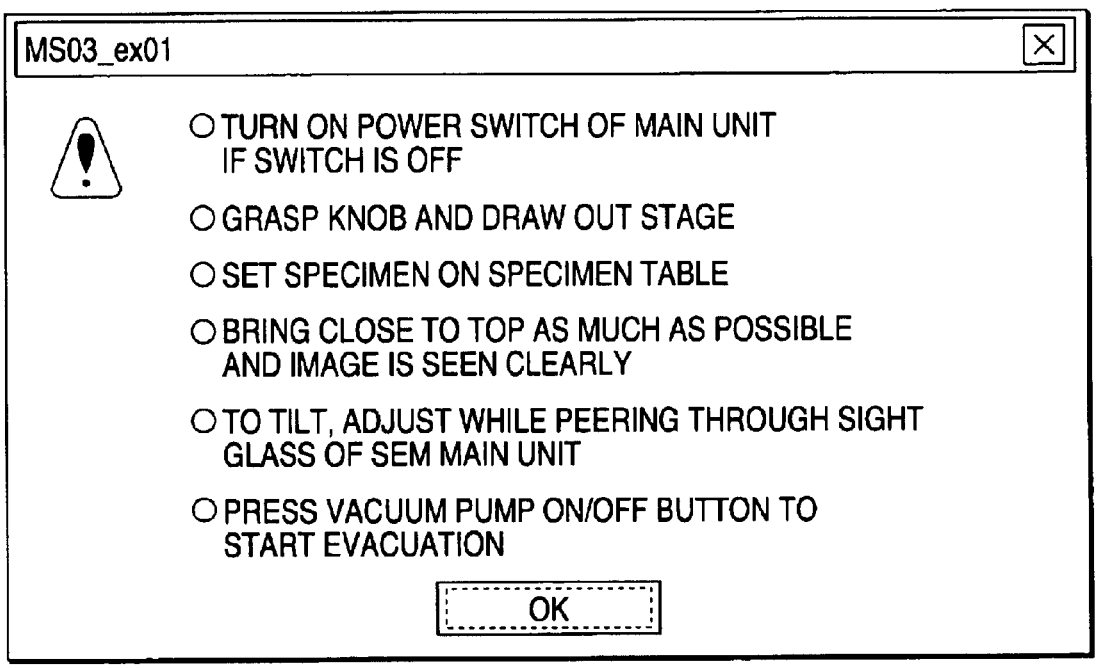
FIG. 5 is an image drawing to show an example of a message screen for giving cautions in operating the electron microscope.

First, when the electron microscope operation program is started, a selection screen in FIG. 2 is displayed on a screen of the computer 1 in FIG. 1. The selection screen displays various operation selection buttons together with the description of the operation contents. The operator selects any desired operation and presses its corresponding button. Here, if the operator presses the AUTO OBSERVATION 40, the screen changes to a screen in FIG. 6 and the auto observation mode is started. In the auto observation mode, necessary setup items are displayed for each screen according to the guidance function. Each setup item is described with text, voice, a still picture of illustration, photo, etc., a moving picture of animation, etc., alone or in combination as required. The necessary setup items can also be highlighted as blinking, reverse display, etc. In addition, a message can also be displayed as a caution for the operator whenever necessary. For example, when a transition is made to the auto observation mode, a message screen as shown in FIG. 5 can be displayed for prompting the operator to check the items to be noted.

Further, warning means may be provided for informing the operator that the entry contents are erroneous when setting not allowed in each setup item is entered. To give a warning, not only a method of displaying a text message, but also a method of producing a warning beep, playing back a voice message, etc., can be used. Limitation can also be placed on a specific item so as to inhibit setting or change for preventing malfunction. Further, an operation item requiring no setting may be suppressed in screen display.

The operator repeats operation of pressing a NEXT button to advance to a setup item on the next screen after termination of setting on each screen, whereby the operator can execute necessary setting step by step for finally acquiring an observation image. To return the setup screen to the preceding screen, the operator presses a BACK button, whereby the operator can again execute setting from the beginning.

[Step S1: Select Material of Specimen]

Figure 6:
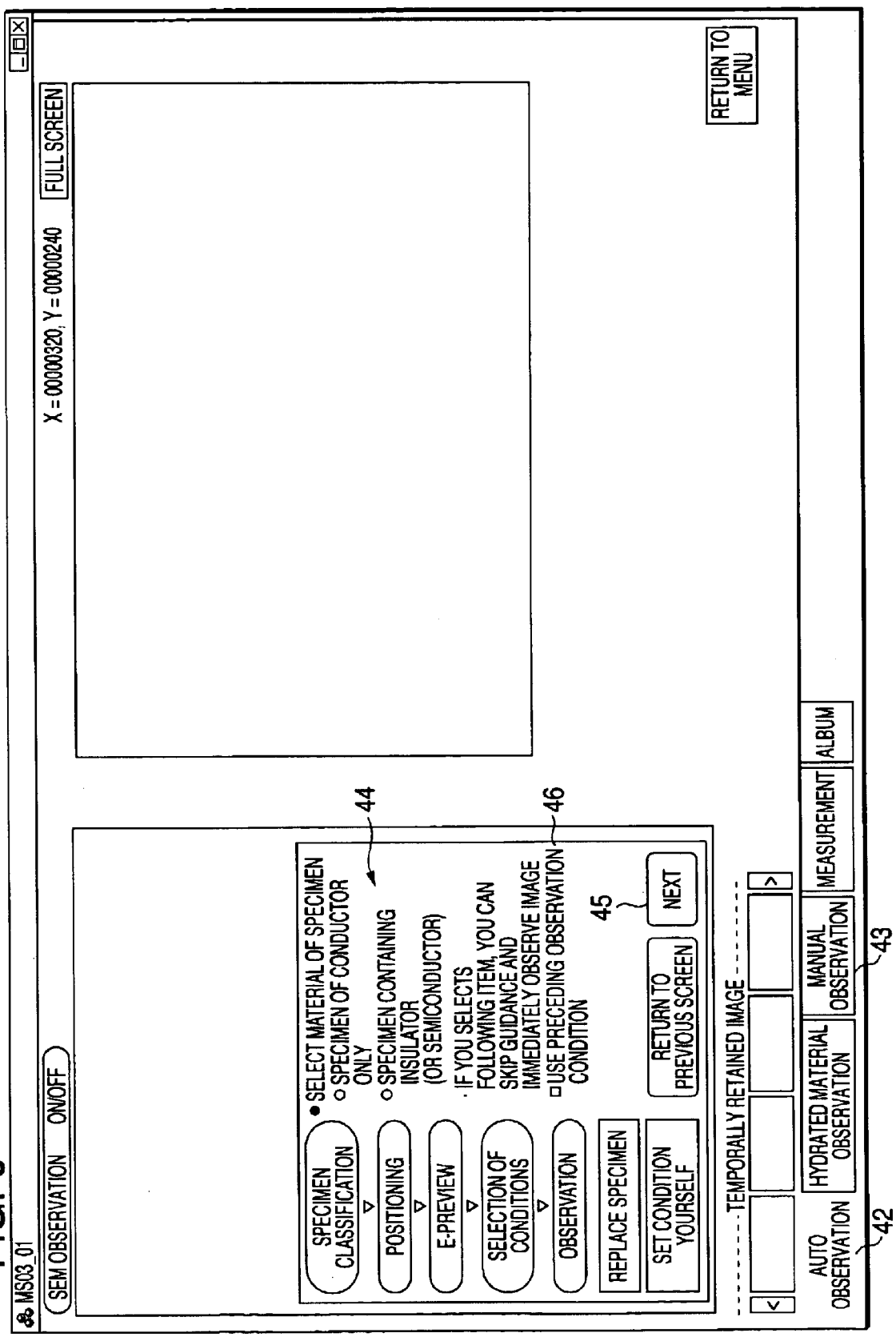
FIG. 6 is an image drawing to show a specimen classification screen in the auto observation mode in the scanning electron microscope operation program according to the embodiment of the invention.

FIG. 6 shows a specimen classification screen provided with a specimen classification field 44 for requesting the operator to select the material of a specimen. The operator uses a radio button to specify whether the specimen whose image is to be observed is made of a conductor only or contains an insulator or a semiconductor. The acceleration voltage and the spot size are determined in response to the electrical conductivity of the specimen. If the specimen is electrically conductive, there is no fear of charge-up, but if the specimen contains an insulator or a semiconductor, there is a fear of occurrence of charge-up and thus care needs to be taken so as not to excessively raise the acceleration voltage. The electron microscope or the computer automatically determines both the acceleration voltage and the spot size in accordance with the selection.

The setting is setting for acquiring an observation image to perform positioning on the next screen and not for acquiring an optimum observation image. To acquire an observation image, an electron beam must be applied under some condition, but the optimum condition cannot be determined at the point in time. The acceleration voltage and the spot size are set to safe values aiming at acquiring an observation image without giving a high priority to the observation image quality so as to make it possible to acquire an observation image whose whole image can be determined to such an extent that positioning can be performed. Further, the magnification is set a low value so that the whole of the image can be acquired. If the operator selects the material of the specimen, the NEXT button 45 is changed from gray-out mode to selectable mode. If the operator presses the NEXT button 45, a transition is made to a positioning screen in FIG. 7, applying an electron beam is started based on the setup acceleration voltage, and image observation at low magnification is conducted.

To conduct image observation under the same image observation condition as the preceding image observation condition, the operator checks a USE PRECEDING IMAGE OBSERVATION CONDITION box 46. If the operator checks the box and presses the NEXT button 45, the operator can skip guidance and immediately advance to image observation.

[Simple Acceleration Voltage and Spot Size Determination Technique]

Here, a technique of simply determining the acceleration voltage and the spot size by the electron microscope or the computer will be discussed. Even for simple observation, it is desirable that several conditions should be satisfied. For example, to observe a specimen easily charged up, the specimen needs to be observed under the condition not charging up the specimen. If the specimen easily undergoes damage such as thermal deformation or evaporation, the specimen must be observed under the condition for preventing damage to the specimen. In addition, the condition needs to be set so as to observe the specimen as clear as possible. Further, in addition to the acceleration voltage and the spot size, all parameters required for observation must be set to actually form an observation image.

As the technique of simply determining the acceleration voltage and the spot size, the following procedure can be used:

[Characteristics of Specimen]

First, the operator specifies conductivity of the specimen. For example, the operator selects the presence or absence of electric conductivity of the specimen. Alternatively, the operator selects semiconductor or mixed specimen.

Further, the operator specifies heat resistance of the specimen. The operator specifies whether or not the specimen becomes easily deformed due to heat and whether or not the specimen contains a component easily evaporated, such as water content. If the specimen is a stable specimen such as metal, there is no problem if an electron beam is applied; if the specimen is an unstable specimen, there is a fear of giving damage to the specimen by electron beam application. Thus, the electron beam application condition is adjusted in response to the nature of the specimen.

The operator also specifies the structure of the specimen. For example, the operator specifies which of lump, powder, granular material, and aggregate of elongated substances such as fibers the specimen is, and condition settings responsive thereto are provided as a temporary setting candidate group. If the specimen is a lump, the operator specifies more detailed conditions such that the specimen has minute asperities on the surface, that the surface is flat, and that coating of gold evaporation, etc., or any other pretreatment is applied to the surface, and conditions appropriate therefor are provided.

Further, a setting group responsive to an observation purpose is provided. As the operator specifies an observation purpose, automatically the corresponding setup value is set. For example, the operator selects the purpose of conducting X-ray element analysis, checking a distribution of the composition making up the specimen, checking an uneven substance, checking the specimen through thin oil content deposited on the specimen surface, or the like, and provided setting group appropriate therefor is used.

Other image observation condition parameters are set in response to the acceleration voltage and the spot size simply set as described above. For example, to adjust the optical axis, namely, adjust the straight line through the centers of the lenses, stops, etc., of the optical system as the line passing through the optical system, appropriate optical axis adjustment values are provided as a table in response to the relationship between the acceleration voltage and the spot size, and the table is referenced, whereby the corresponding optical axis adjustment is made.

To set the acceleration voltage and the spot size, not only the method of adjusting both the acceleration voltage and the spot size, but also a method of adjusting the other with one set to a fixed value may be adopted.

In addition, the specimen can also be observed with both the acceleration voltage and the spot size set to fixed values rather than according to the above-described technique. At the time, it is desirable that the acceleration voltage and the spot size should be set to acceptable values with a view to acquiring an observation image rather than to acquiring an optimum image.

[Step S2: Perform Observation Positioning and Magnification Adjustment]

Figure 7:
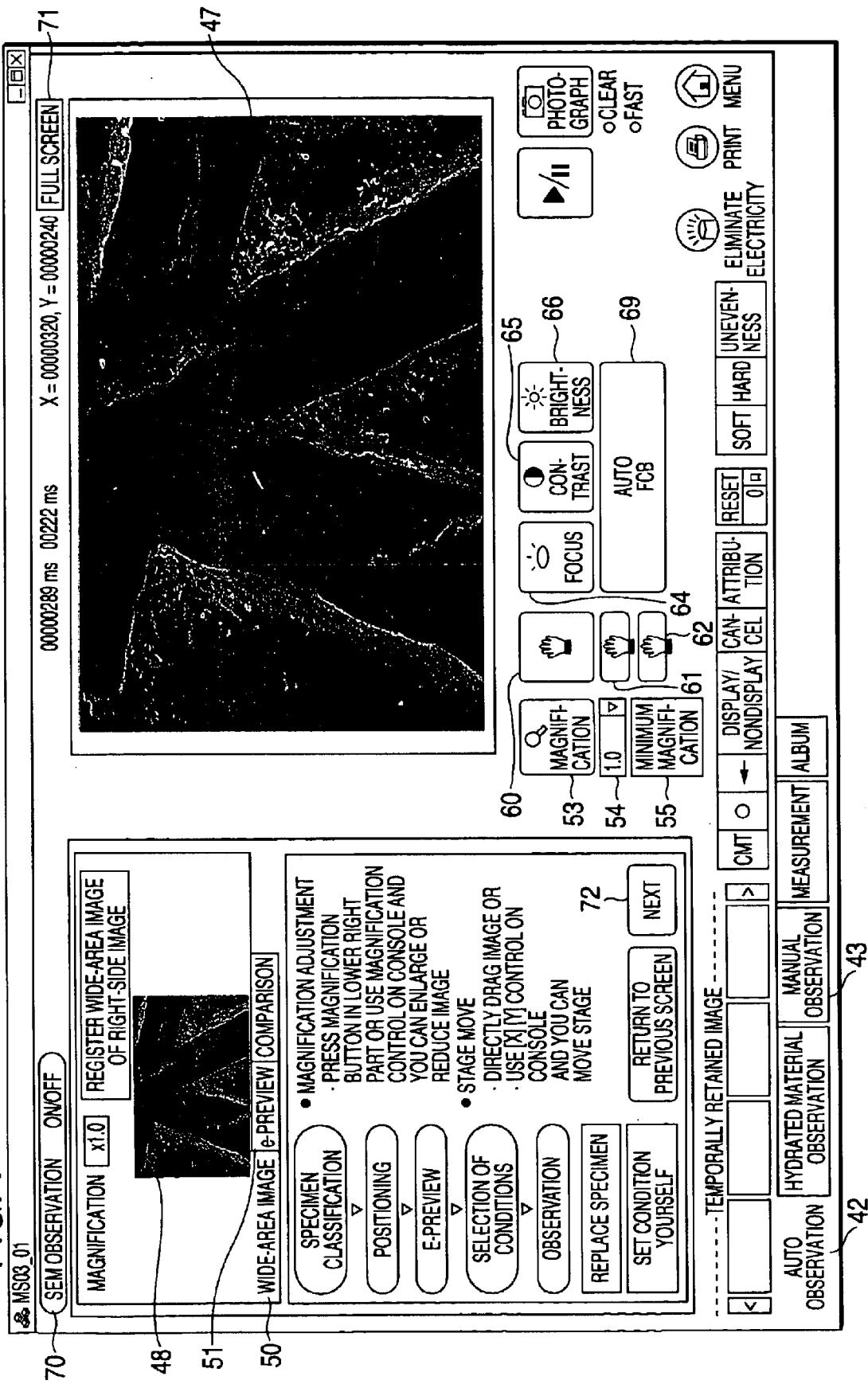
FIG. 7 is an image drawing to show a positioning screen in the auto observation mode in the scanning electron microscope operation program according to the embodiment of the invention.
Figure 8:
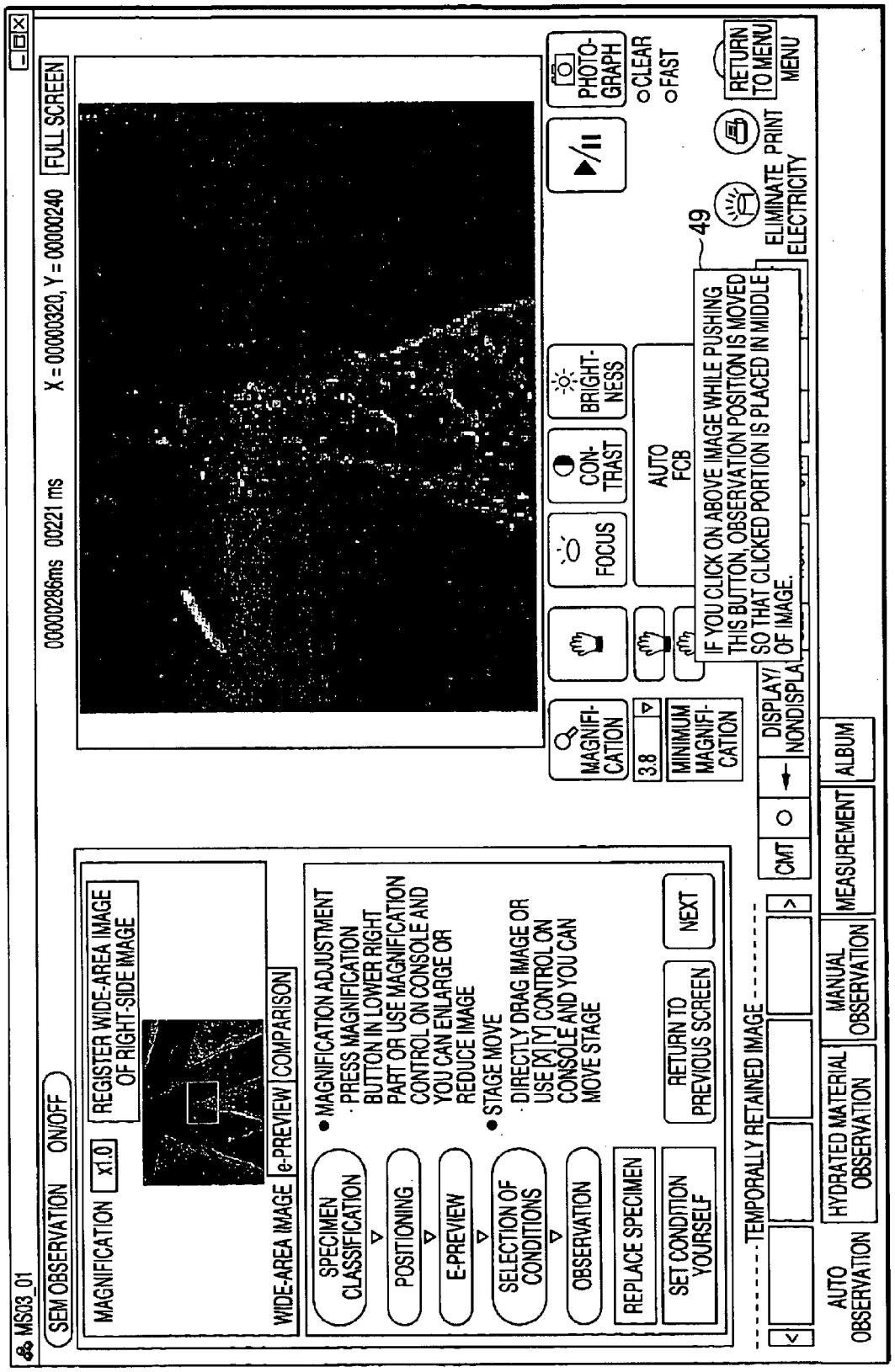
FIG. 8 is an image drawing to show a tool chip function in the scanning electron microscope operation program according to the embodiment of the invention.
Figure 9:
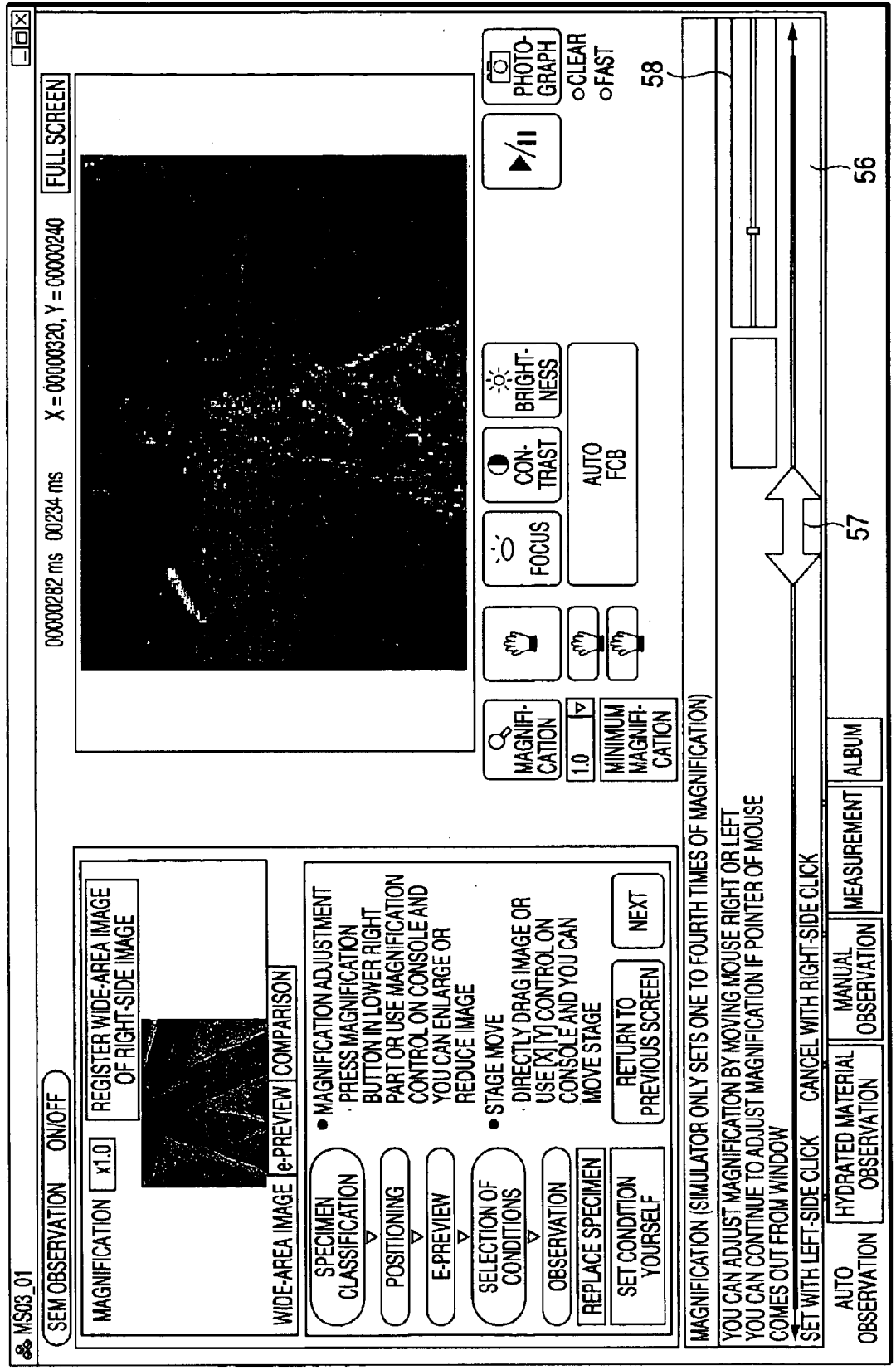
FIG. 9 is an image drawing to show a state in which a first magnification button is operated on the positioning screen in FIG. 7.

FIG. 7 shows a positioning screen for requesting the operator to manually set observation positioning and magnification. The screen in FIG. 7 comprises a first display section 47 to produce main display and a second display section 48 of an auxiliary display section for setting display on the first display section 47. Various setting buttons are placed on the screen. As shown in FIG. 8, a mouse pointer is put on each button, whereby the function description and hint of the button are displayed on a chip screen 49 by a tool chip function. Further, the button or item on which the mouse pointer is put can be highlighted as a frame is displayed or an image of pressing the button is displayed, so that the current item attempted to select can also be clarified.

The display contents of the second display section 48 are switched between a wide-area image 50 and e-preview 51 as a tab is selected. In the example in FIG. 7, for the second display section 48, wide-area image 50 is selected for displaying the whole of an observation image based on the entry and setting in FIG. 6. On the other hand, the first display section 47 displays an image provided by setting and processing the image on the second display section 48. In the example in FIG. 8, a part of the second display section 48 is displayed on an enlarged scale.

[Magnification Adjustment]

The magnification is determined in the first display section 47 in FIG. 7. The operator determines any desired magnification while checking an observation image displayed on the first display section 47. In the example in FIG. 7, the magnification value is a relative value indicating the ratio of the size displayed on the first display section 47 to the size displayed on the second display section 48. For example, when the same image as on the second display section 48 is displayed on the first display section 47, the magnification value becomes 1. However, the display of the magnification is not limited to the example; for example, the magnification may be displayed as an absolute enlargement ratio to the size of the specimen.

To change the magnification, the operator uses a magnification button of a magnification adjustment section. In the example in FIG. 7, first to third buttons 53, 54, and 55 are provided. If the operator presses the first magnification button 53 given an icon shaped like a magnifying glass, a screen in FIG. 9 appears and a slider 56 is displayed as a subwindow. As the operator moves an arrow 56 displayed on the slider 56 through input means, the magnification is changed continuously. For example, as the operator moves the slider 56 to the right with the mouse, the image is enlarged; as the operator moves the slider 56 to the left, the image is reduced. Following the specification, the observation image displayed on the first display section 47 is enlarged or reduced in real time. The drawing speed may vary and the image may be displayed with a small delay depending on the operation processing capability of the electron microscope or the computer. At this time, the mouse pointer need not be set onto the slider 56 and the operator can operate the slider 56 simply by moving the mouse to the left or right. A range display section 58 that can be enlarged and reduced is displayed in the upper right corner of the subwindow and indicates what position of the enlargement and reduction range the magnification of the current image being displayed on the first display section 47 is at.

Figure 10:
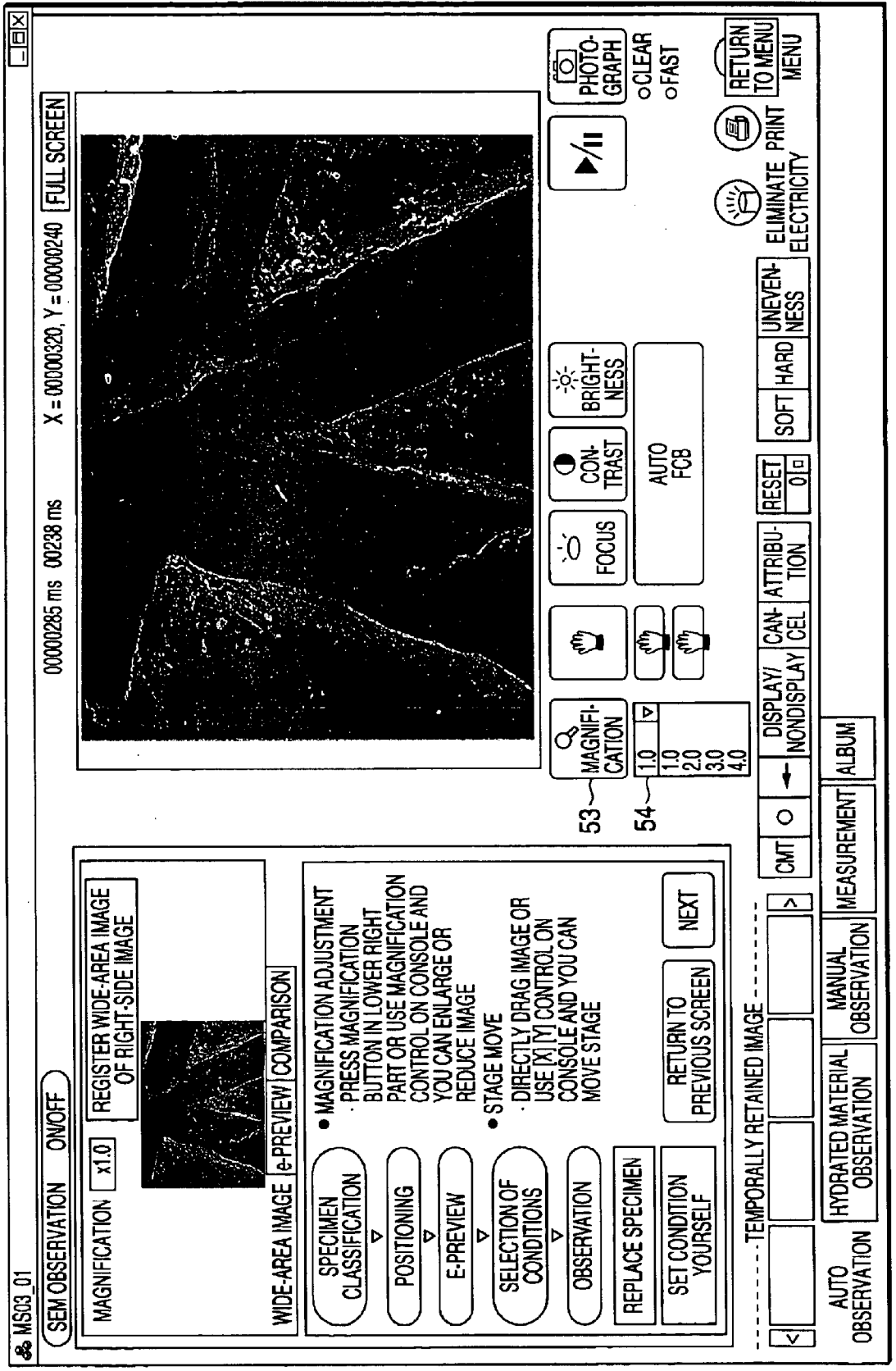
FIG. 10 is an image drawing to show a state in which a drop-down menu is displayed by operating a second magnification button on the positioning screen in FIG. 7.
Figure 11:
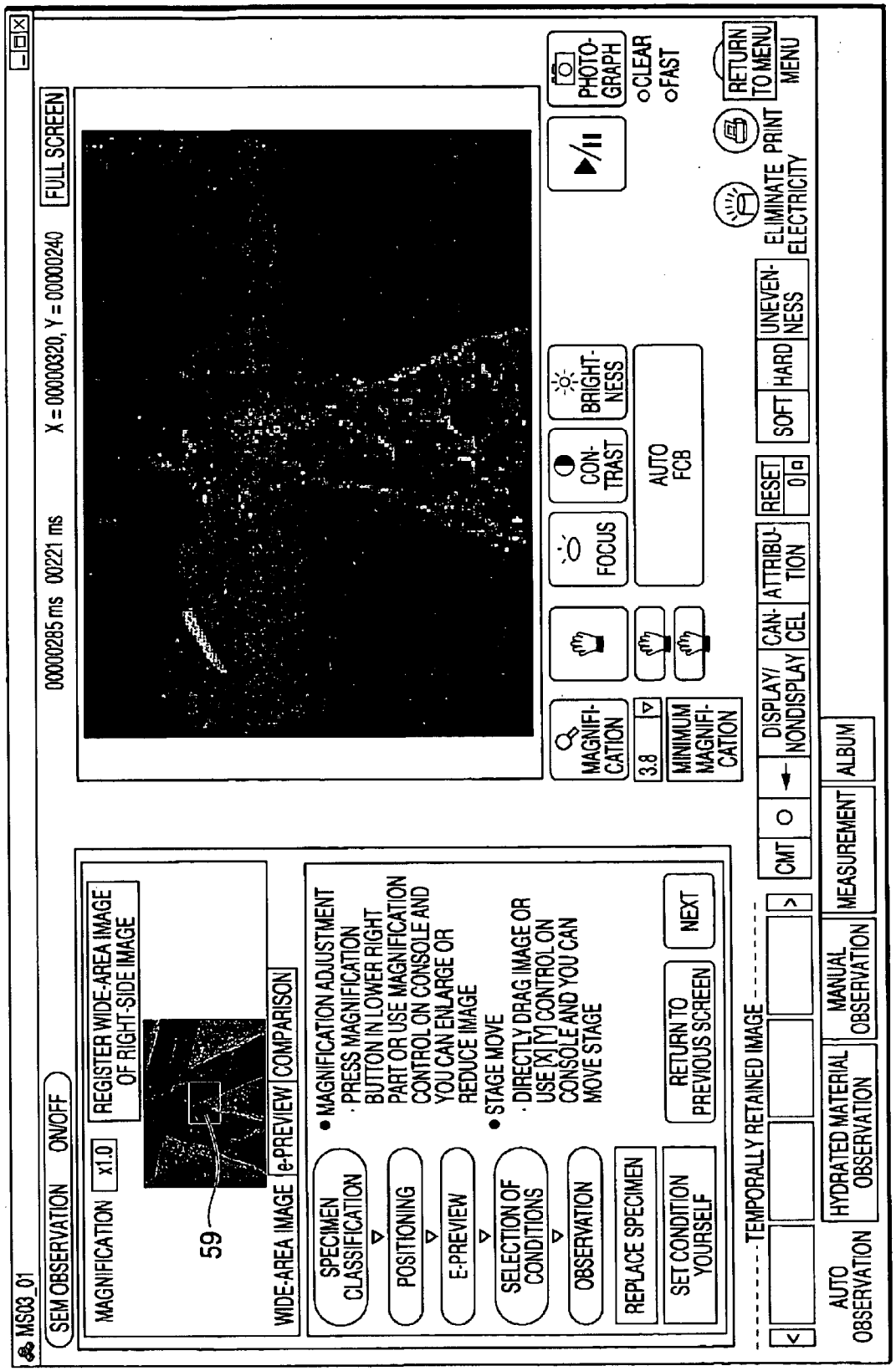
FIG. 11 is an image drawing to show a state in which an enlarged image is displayed on a first display section on the positioning screen in FIG. 7.

The second magnification button 54 displays the magnification in a numeric value. The second magnification button 54 enables the operator to select a predetermined magnification out of a drop-down menu as shown in FIG. 10 or directly enter any desired magnification value in a numeric value. If the operator changes the magnification by operating the first magnification button 53 or the third magnification button 55, the second magnification button 54 also displays the magnification of the current observation image displayed on the first display section 47.

If the operator presses the third magnification button 55, namely, MINIMUM MAGNIFICATION button, a predetermined minimum magnification (for example, 1) is set, whereby immediately the display can be restored to display of the whole image.

If the image is displayed on an enlarged scale on the first display section 47, what part of the image on the second display section 48 is enlarged on the first display section 47 is indicated as the area surrounded by a rectangular frame 59 on the second display section 48. Accordingly, the operator can check what position is displayed at present, and can move to any desired position while checking the second display section 48. In the example in FIG. 7, first to third move buttons 60, 61, and 62 are provided as move buttons each with a palm-shaped icon. If the operator clicks on the first move button 60, the cursor changes like a palm shape on the first display section 47, and the operator can press the left button of the mouse at any desired position and drag, thereby directly grasping the screen and moving. If the operator releases the left button after moving to any desired position, the move mode is released.

The second move button 61 can be used to move with the specified position as the center. If the operator presses the second move button 61, an automatic move is made so that an image with an arbitrary position clicked on the first display section 47 as the center is displayed.

Figure 12:
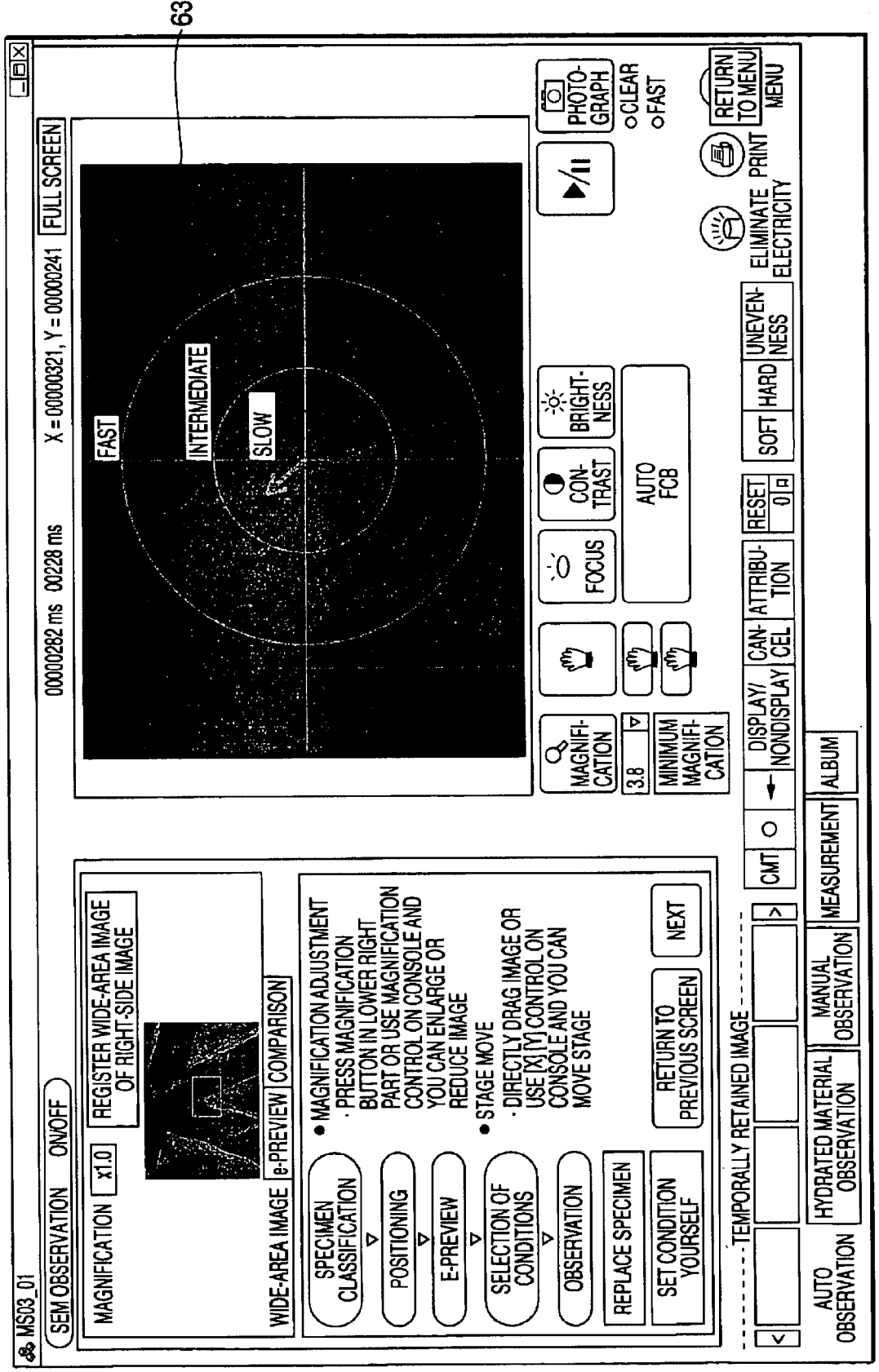
FIG. 12 is an image drawing to show a state in which a third move button is operated on the positioning screen in FIG. 7.
Figure 13:
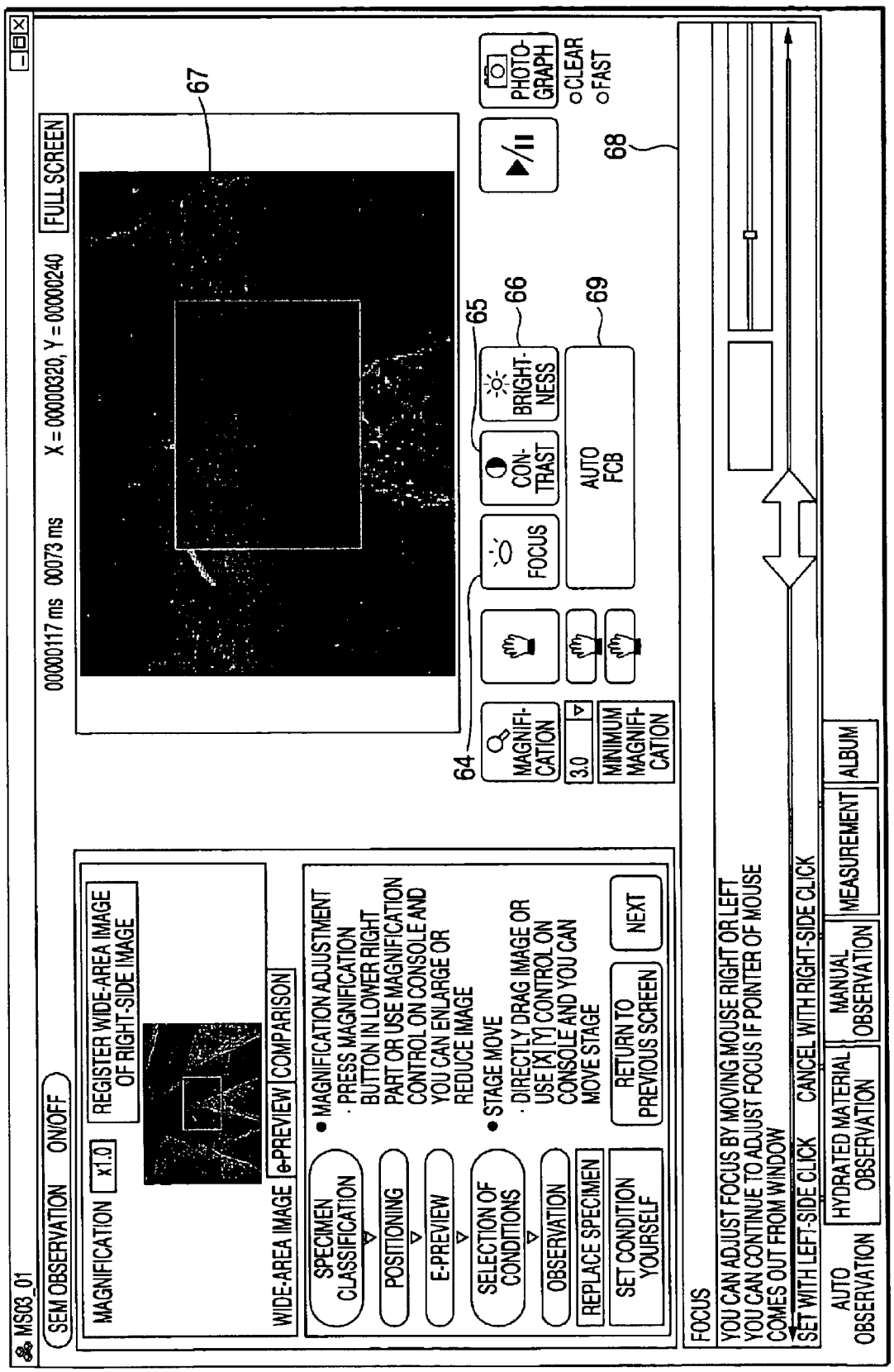
FIG. 13 is an image drawing to show a state in which focus adjustment is made on the positioning screen in FIG. 7.

Further, the third move button 62 enables the operator to specify the screen move direction and move speed. If the operator presses the third move button 62, the cursor changes like a target on the first display section 47. While the operator continues to press the left button in this state, a target-like grid 63 as shown in FIG. 12 is displayed. The target-like grid 63 is displayed almost at the center of the first display section 47, and the screen is moved in the direction in which the mouse pointer, etc., is positioned relative to the center of the target-like grid 63. The move speed changes in accordance with the distance from the center; the nearer to the center, the slower the move and the more distant from the center, the faster the move. Accordingly, the operator can easily operate screen move in any desired direction.

The described observation positioning is performed as the specimen table on which a specimen is placed is moved. As the operator operates the move button, the specimen table is moved in the X direction and the Y direction. However, to move in the display range on the second display section 48, display is possible without moving the specimen table.

To position an observation image and move the observation visual field, the method is not limited to the method of physically moving the specimen table; for example, a method of shifting the scan position of an electron beam applied from the electron gun (image shift) can also be used. Alternatively, both methods can also be used in combination or a method of once inputting image data in a wide range and then processing the data by software can also be used. In this method, the data is once input and is processed and thus the observation position can be moved by software and the method has the advantage that it does not involve hardware move of moving the specimen table or scanning an electron beam. To previously input large image data, for example, a method of acquiring a plurality of pieces of image data at various positions and concatenating the image data, thereby acquiring wide-area image data is available. Alternatively, image data is acquired at low magnification, whereby the acquired area can be taken large.

[Focus Adjustment]

The operator uses a FOCUS button 64, a CONTRAST button 65, and a BRIGHTNESS button 66 to adjust focus, contrast, and brightness respectively as required. If the operator presses the FOCUS button 64, an area surrounded by a frame 67 is specified on the first display section 47, and a slider 68 is displayed as a subwindow. The operator moves the slider 68 left and right with a mouse, etc., and makes focus adjustment in the area in the frame in a similar manner to that described above. At this time, only the area surrounded by the frame 67 undergoes focus adjustment and the area outside the frame does not change, so that the operator can easily check the focus adjustment effect in comparison. If the operator clicks the right button of the mouse and terminates the focus adjustment, the frame 67 disappears and the focus adjustment is executed in the whole area of the first display section 47. Likewise, the operator can use the CONTRAST button 65 to adjust the contrast with the slider and can use the BRIGHTNESS button 66 to adjust the brightness with the slider.

Further, the focus, the contrast, and the brightness can also be adjusted automatically. If the operator presses an Auto FCB button 69, the optimum condition for the image being displayed on the first display section 47 is computed by image processing, and an automatically adjusted image is displayed on the first display section 47.

Further, a SEM OBSERVATION ON/OFF button 70 indicating that SEM observation is on is displayed in the upper left corner of the screen in FIG. 7. The operator can switch on and off SEM observation by pressing the button 70.

Further, a FULL SCREEN button 71 is provided in the upper right corner of the screen in FIG. 7. As the operator presses the button 71, the whole screen can be used as the area of the first display section 47.

Figure 14:
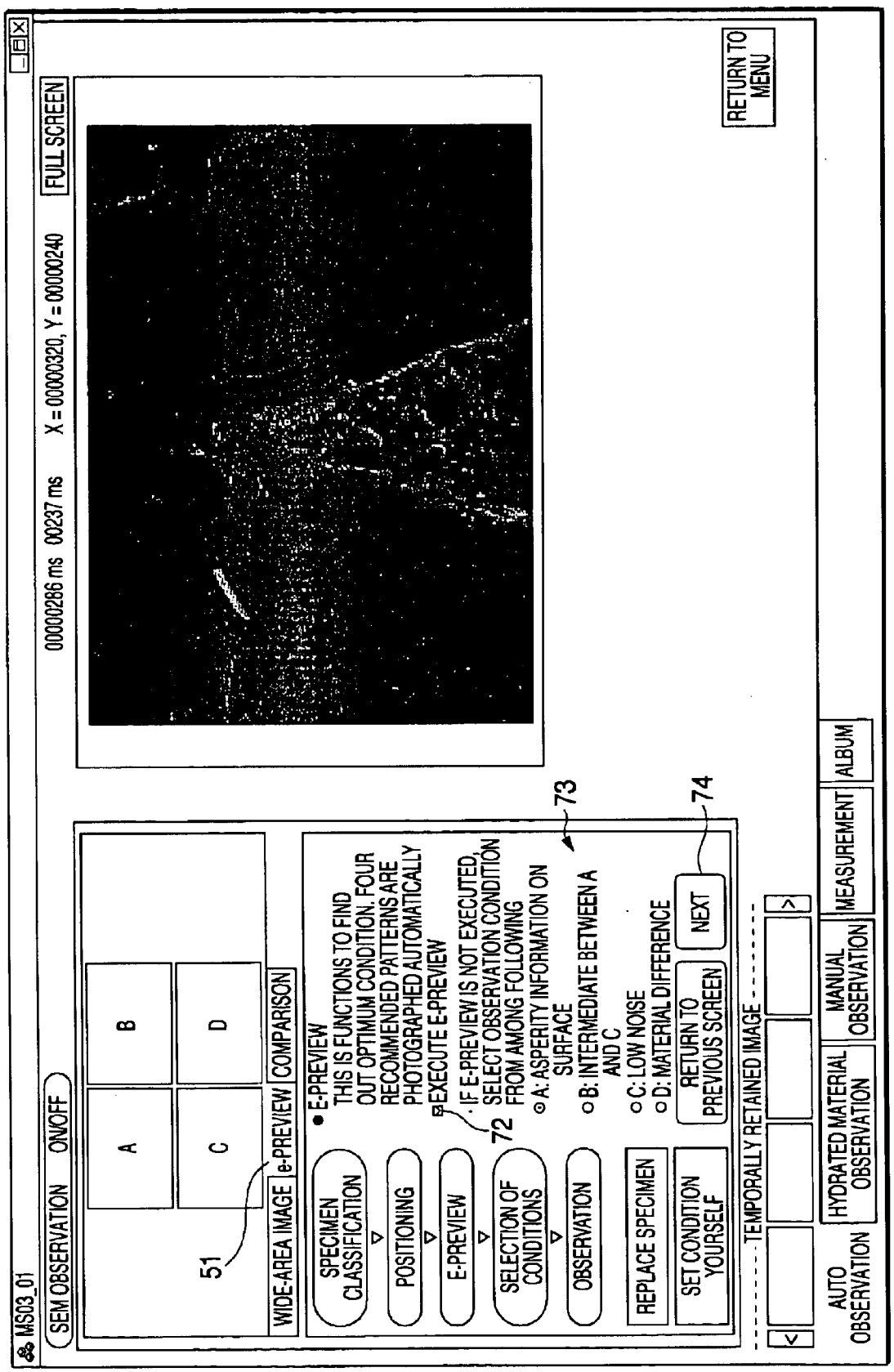
FIG. 14 is an image drawing to show an e-preview screen in the auto observation mode in the scanning electron microscope operation program according to the embodiment of the invention.

If the operator presses a NEXT button 72 after the positioning and magnification adjustment are thus performed, the screen is switched to a screen in FIG. 14.

[Step S3: Select Image Observation Condition]

Figure 15:
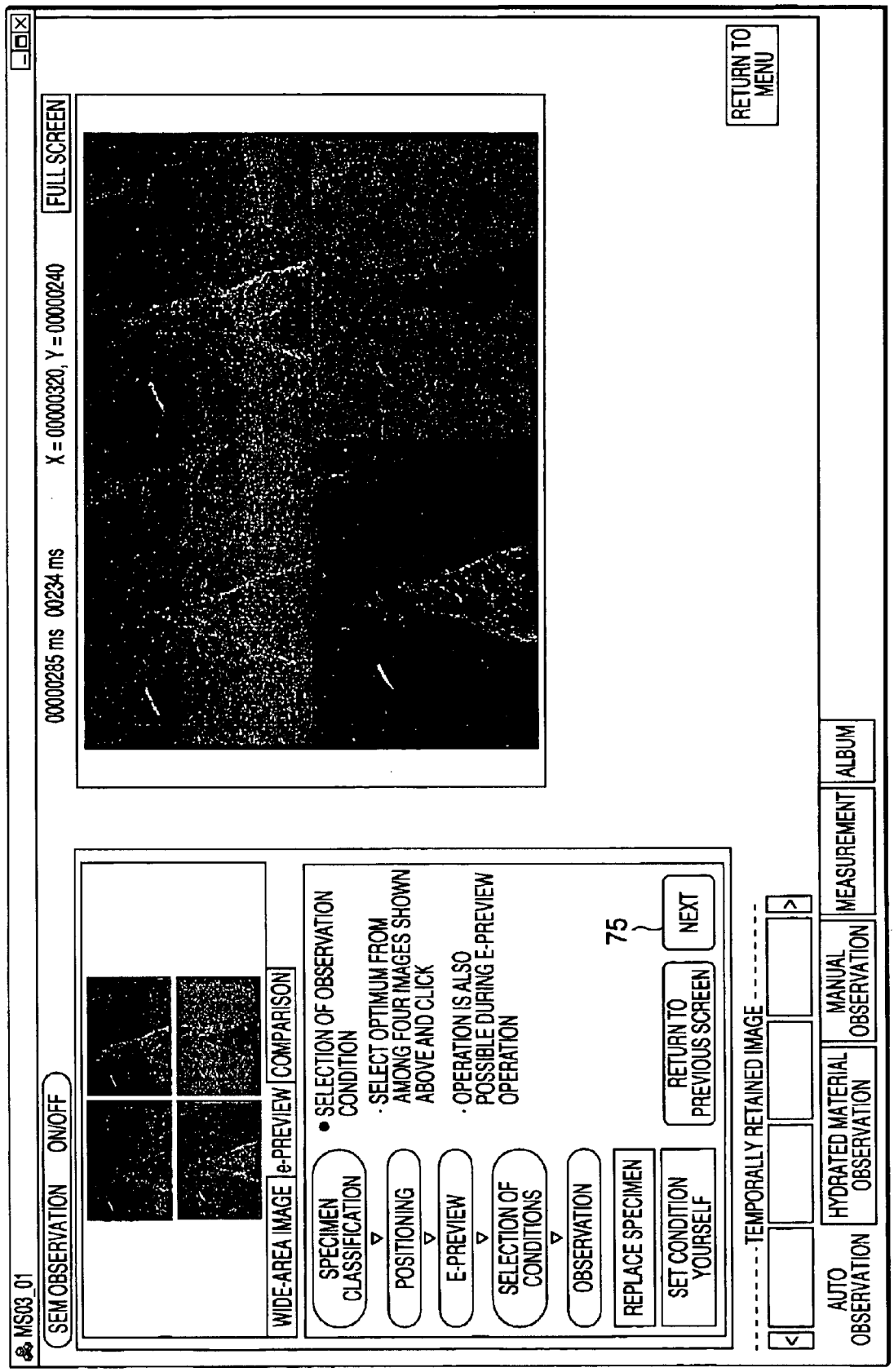
FIG. 15 is an image drawing to show a condition selection screen in the auto observation mode in the scanning electron microscope operation program according to the embodiment of the invention.

On the screen in FIG. 14, the operator selects image observation condition at the observation position and adjustment determined as described above. Here, the operator specifies execution of e-preview for setting a plurality of observation conditions and acquiring a plurality of observation images or selecting only one image observation condition and acquiring one observation image. To execute e-preview, the operator checks a box 72 of EXECUTE E-PREVIEW. FIGS. 14 and 15 show an example of acquiring four preview images of A to D and displaying the images on the second display section 48. The observation conditions to acquire the preview images A to D are selected from among candidates of observation conditions estimated to be appropriate for the specimen to be observed by the electron microscope or the computer. Particularly, specification as to whether the detector to be used is a secondary electron detector or a reflection electron detector and what value the acceleration voltage is set to become important factors. In the example in FIGS. 15, A, B, and C of the preview images A to D indicate secondary electron images and D indicates a reflection electron image. However, the combination of the secondary and reflection electron images is not limited to the example; all may be secondary electron images or reflection electron images or one secondary electron image may be applied with the remainder as reflection electron images. Which detector is to be used is specified appropriately in response to the image observation condition, the purpose of image observation, the operator's intention, etc.

In the example in FIG. 14, the observation condition for the preview image A is set with a view to acquiring fine asperity information on the surface of the specimen, the observation condition for the preview image C is set with a view to observing the specimen with noise suppressed, and the observation condition for the preview image B is set as an intermediate condition between A and C. The observation condition for the preview image D is set with a view to determining the specimen material difference.

The specimen is observed with the observation condition changed in the direction of increasing the acceleration voltage to avoid charge up. To acquire the preview images in the order of A to D, the acceleration voltage becomes higher from A to D. After detection with secondary electron detector, observation is conducted with reflection electron detector. For example, reflection electron detector is used as the preview image D.

Figure 16:
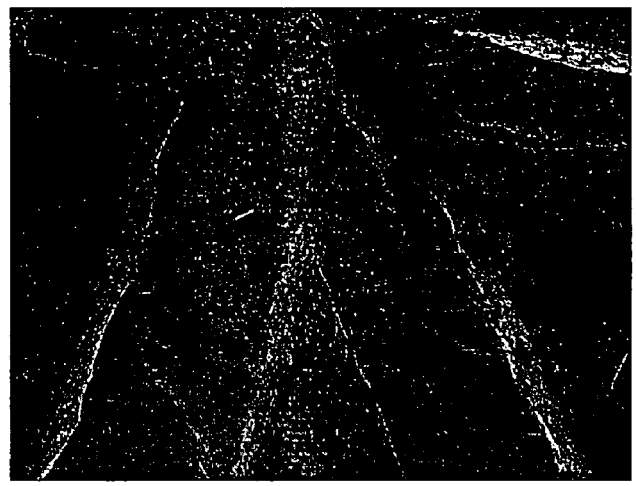
FIG. 16 is an image drawing of observing one-yen coin at magnification of 100 at acceleration voltage 2 kV using secondary electron detector.
Figure 17:
FIG. 17 is an image drawing of observing one-yen coin at magnification of 100 at acceleration voltage 5 kV using secondary electron detector.
Figure 18:
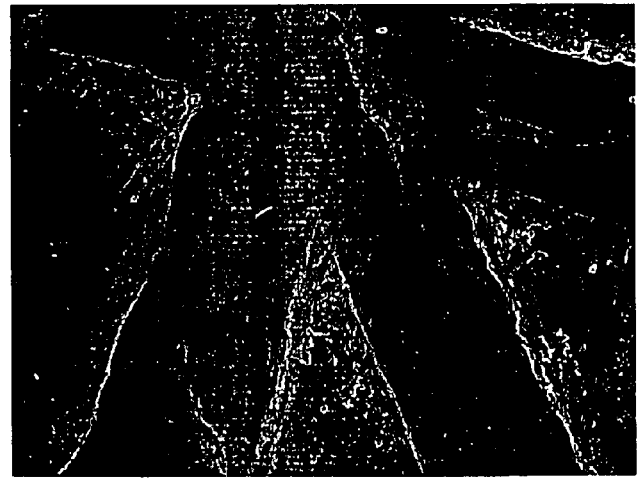
FIG. 18 is an image drawing of observing one-yen coin at magnification of 100 at acceleration voltage 20 kV using secondary electron detector.
Figure 19:
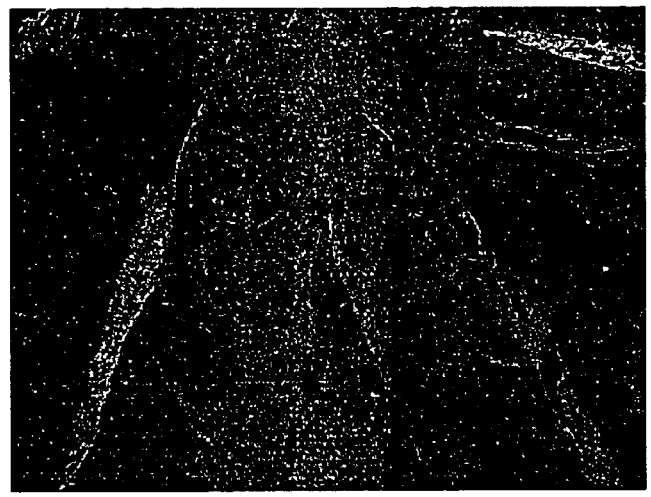
FIG. 19 is an image drawing of observing one-yen coin at magnification of 100 at acceleration voltage 20 kV using reflection electron detector.

FIGS. 16 to 23 show examples of e-preview. FIGS. 16 to 19 show examples of measurement on a one-yen coin as a specimen at magnification of 100, and FIGS. 20 to 23 show examples of measurement on the cross section of a through hole made in a glass epoxy board at magnification of 500. FIG. 16 shows an example of observation at acceleration voltage 2 kV using secondary electron detector; it is seen that up to fine asperities on the surface of the specimen can be observed. FIG. 17 shows an example of observation at acceleration voltage 5 kV with secondary electron detector, and FIG. 18 shows an example of observation at acceleration voltage 20 kV with secondary electron detector. Particularly, in FIG. 18, the asperities of the specimen can be observed through thin oil content on the surface. If the secondary electron detector is thus used as the detector, the asperities on the surface can be observed. Further, FIG. 19 shows an example of observation at acceleration voltage 20 kV with reflection electron detector; the difference between compositions of garbage accumulated in gaps of aluminum can be checked. Thus, the composition of the specimen rather than asperities on the surface is made clear with the reflection electron detector.

Figure 20:
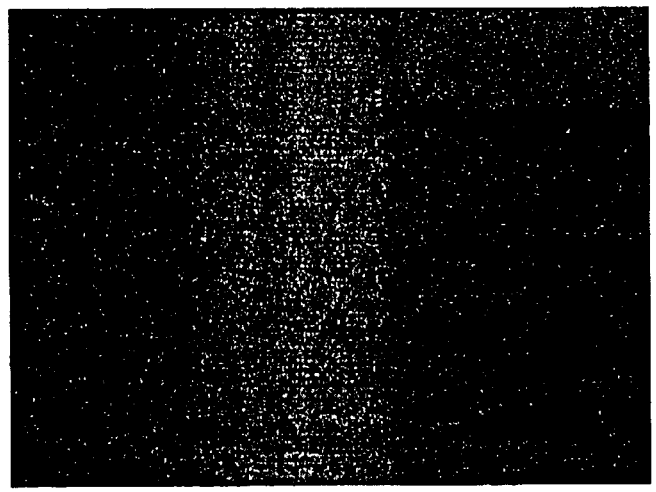
FIG. 20 is an image drawing of observing the cross section of glass epoxy board at magnification of 500 at acceleration voltage 0.8 kV using secondary electron detector.
Figure 21:
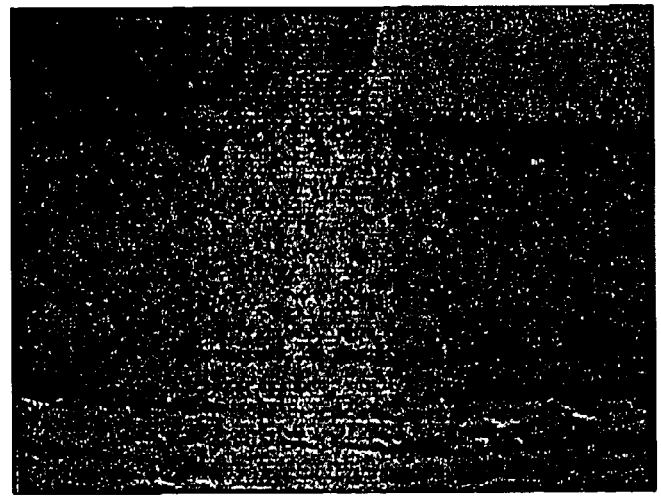
FIG. 21 is an image drawing of observing the cross section of glass epoxy board at magnification of 500 at acceleration voltage 1.2 kV using secondary electron detector.
Figure 22:
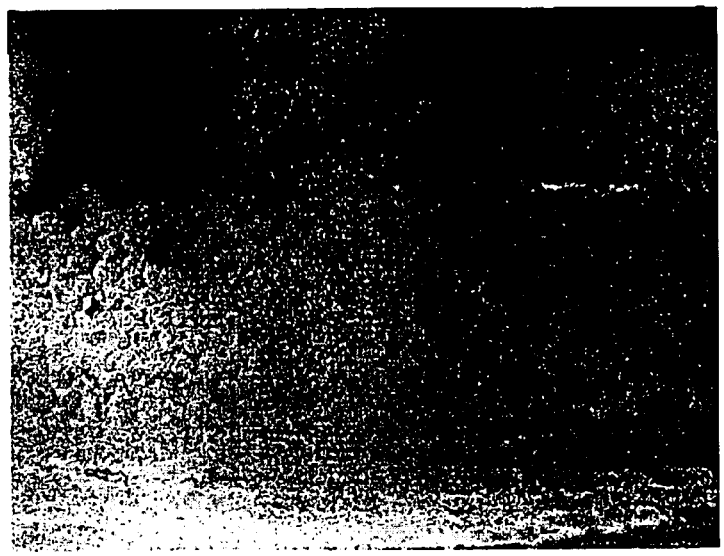
FIG. 22 is an image drawing of observing the cross section of glass epoxy board at magnification of 500 at acceleration voltage 1.6 kV using secondary electron detector.
Figure 23:
FIG. 23 is an image drawing of observing the cross section of glass epoxy board at magnification of 500 at acceleration voltage 2.0 kV using secondary electron detector.
Figure 24:
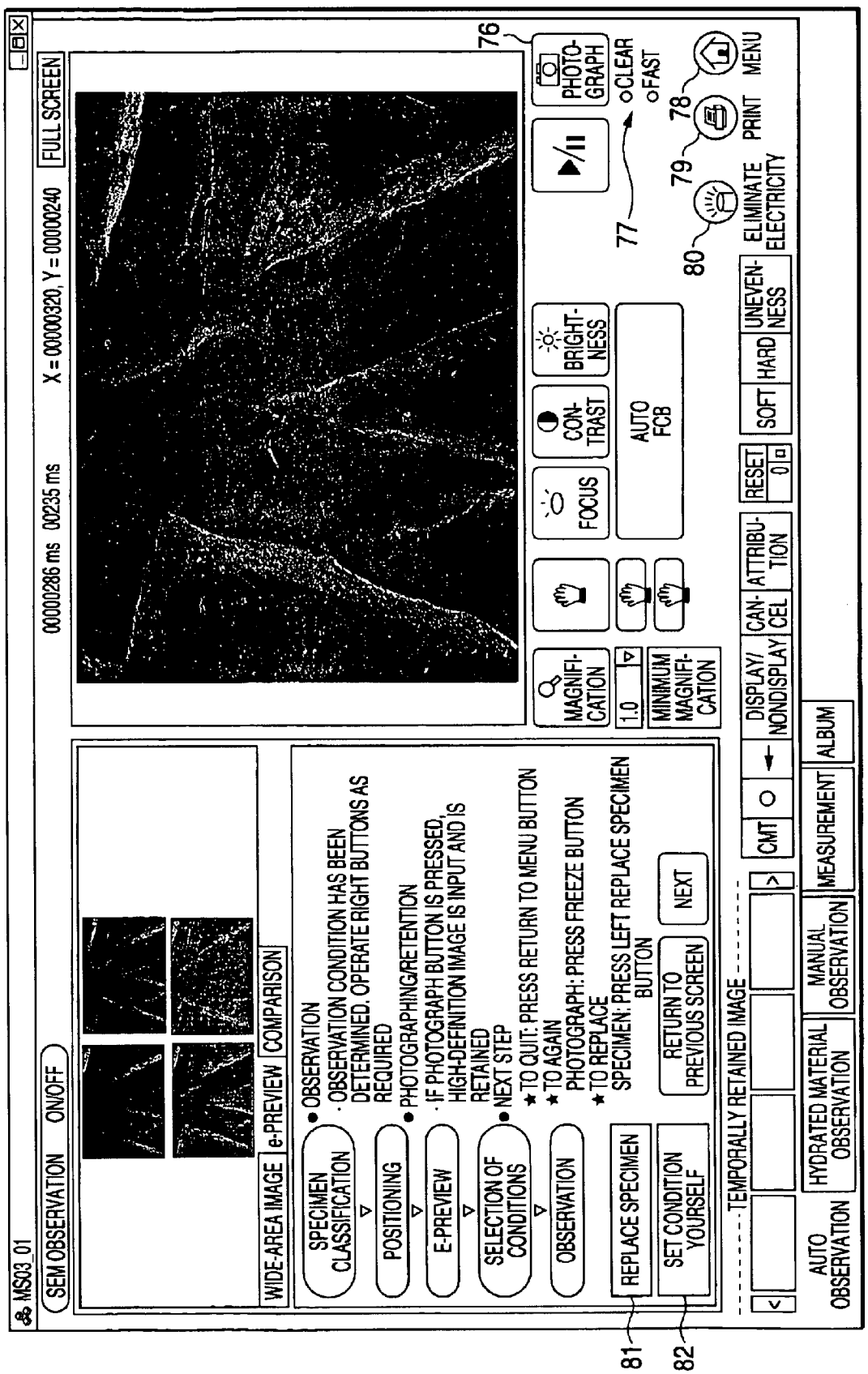
FIG. 24 is an image drawing to show an observation screen in the auto observation mode in the scanning electron microscope operation program according to the embodiment of the invention.

FIGS. 20 to 23 show examples of observation while acceleration voltage is raised using secondary electron detector; the acceleration voltage in FIG. 20 is 0.8 kV, that in FIG. 21 is 1.2 kV, that in FIG. 22 is 1.6 kV, and that in FIG. 23 is 2.0 kV. It can be recognized in the figures that as the acceleration voltage is raised, charge-up occurs and image formation is disordered.

However, the settings are shown by way of example, and can be changed appropriately in response to the specimen and the observation purpose, needless to say. For example, all are observed with secondary electron detector, observation with reflection electron detector is increased, or the number of preview images is increased or decreased.

On the other hand, if e-preview is not executed, the operator selects any desired image observation condition out of an image observation condition selection field 73. As options in the image observation condition selection field 73, a combination of observation conditions which seems to be optimum is automatically computed and presented by the electron microscope or the computer. Here, the options in the image observation condition selection field 73 correspond to the preview images A to D in e-preview described above. If the operator selects any desired observation condition and presses a NEXT button 74, one preview image formed under the selected observation condition is displayed on the second display section 48. In this case, only one image is drawn and thus preview requires a short time. This can be used when the observation condition to be selected is determined, for example, when a similar specimen was observed and the same condition as the observation condition applied at the previous observation time is set, when an already observed specimen is again to be observed, etc.

If the operator checks the box 72 of EXECUTE E-PREVIEW, the image observation condition selection field 73 is grayed out and becomes unselectable. Thus, it is made impossible to select an unnecessary item, so that malfunction can be prevented.

[Condition Selection]

If the operator checks the box 72 of EXECUTE E-PREVIEW and presses the NEXT button 74, the screen changes to a condition selection screen in FIG. 15 and the e-preview operation is started. At this time, the second display section 48 is switched to E-PREVIEW 51 for displaying a plurality of preview images. As the e-preview operation is performed, preview images are drawn in order. It takes several seconds to several ten seconds in drawing each preview image. As each preview image, a distinctive observation image is displayed in response to the corresponding observation condition. The operator selects any desired image from among the preview images displayed on the second display section 48.

In the example in FIG. 15, the four preview images A, B, C, and D are displayed. If the operator superposes the mouse pointer on each preview screen, a description is chip-displayed. For example, the numbers and the features of the preview images, the acceleration voltage, and the like are displayed in such a manner that "A: Easy on specimen although resolution is low (acceleration voltage 2 kV)," "B: Intermediate between A and C (acceleration voltage 5 kV)," "C: Hard on specimen although resolution is high (acceleration voltage 20 kV)," and "D: Material difference is easy to understand (acceleration voltage 20 kV)."

If the operator clicks on any preview image for selection, the selected observation image is displayed on the first display section 47, so that the operator can check the observation image in more detail as an enlarged image. If the operator thus selects any desired preview image and then presses a NEXT button 75, the screen advances to an observation screen in FIG. 24.

The e-preview operation takes a time to some extent until display of all preview images is complete. Thus, when any desired preview image is displayed, if other preview images are not yet displayed, the operator can select the desired preview image and advance to the next step or can select even a preview image not yet displayed.

As for astigmatism correction, automatic adjustment may not well function and if the automatic adjustment results in failure and a preview image cannot be acquired, it is made impossible to make a comparison with any other preview image. Thus, a method of skipping astigmatism correction can be used. For example, the initial value of astigmatism is used or astigmatism is fixed to a predetermined value which seems to be appropriate, or to skip astigmatism correction, the values of astigmatism are preset in a table in response to other image observation conditions, such as the detector type, the acceleration voltage, and the spot size, and the appropriate astigmatism value is set by referencing the table. Alternatively, the magnification is limited, for example, to 10000 times at the maximum, whereby the fear of occurrence of astigmatism can be avoided.

[Step S4: Pick Up Image and Perform Any Desired Operation]

An observation image is displayed on the first display section 47 based on the preview image condition thus selected. Additional adjustment can be made to the acquired observation image. The adjustable items include magnification, positioning, focus adjustment, contrast adjustment, brightness adjustment, and the like similar to those described above.

When the desired observation image is acquired, further any desired operation is performed for the acquired image. For example, image photographing, retention, print, dimension measurement, etc., can be performed. If the operator presses a PHOTOGRAPH button 76 on the screen in FIG. 24, the observation image being displayed is input and the image data is retained on a medium such as a hard disk of the computer as a digital signal. A radio button 77 for selecting either CLEAR or FAST is provided below the PHOTOGRAPH button 76. The term "CLEAR" mentioned here is used to mean that it takes time in scanning the electron beam applied to the specimen (for example, 60 seconds) for inputting a signal good in S/N ratio of secondary electrons or reflection electrons. The term "FAST" mentioned here is used to mean that it takes short time in scanning the electron beam applied to the specimen (for example, 30 seconds) for inputting a signal with the processing time given a high priority accordingly. If CLEAR is selected, the observation image is retained as image data in higher definition. If FAST is selected, the precision of the image data is a little degraded, but the image data can be retained at higher speed. As the number of pixels of the image data to be retained, any desired size of 640×480 pixels, 1280×960 pixels, 512×512 pixels, 1024×1024 pixels, 2048×2048 pixels, etc., can be used in response to the use purpose.

Further, the next operation is selected as required. If the operator again presses the PHOTOGRAPH button 76, photographing can be again conducted. If the operator presses a RETURN TO MENU button 78 provided in the lower right corner of the screen in FIG. 24, the screen returns to the menu screen in FIG. 2. A PRINT button 79 is placed at the left of the RETURN TO MENU button 78 and enables the operator to print on the printer 29 connected to the computer 1 or the electron microscope. An ELIMINATE ELECTRICITY button 80 is placed at the left of the PRINT button 79 and enables electricity to be eliminated in a state in which the specimen is charged up.

[Replace Specimen]

To replace the specimen and conduct image observation, the operator presses a REPLACE SPECIMEN button 81 placed at the left of the screen. The guidance procedure is again started from the beginning.

[Set Condition Yourself]

Figure 25:
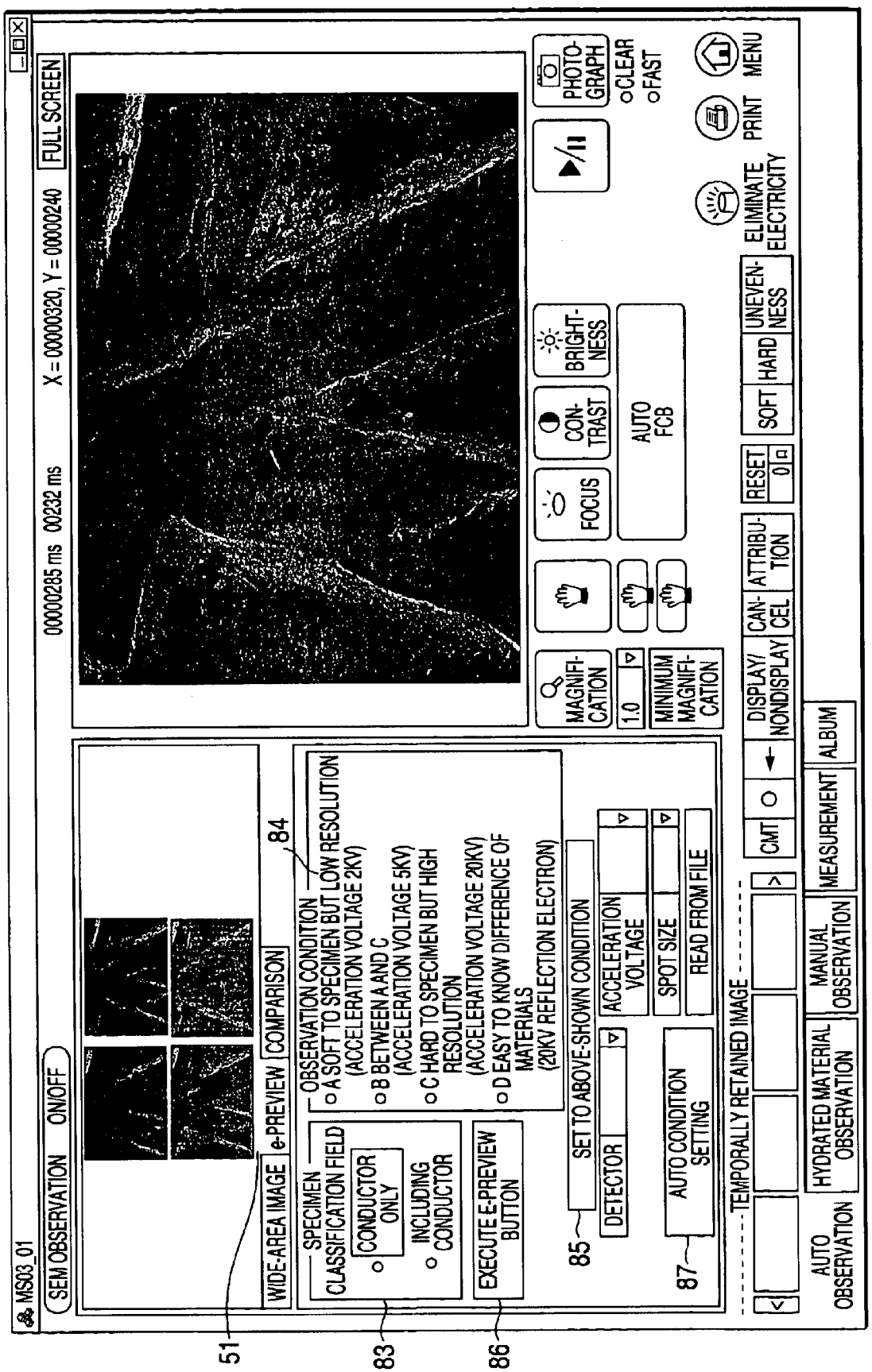
FIG. 25 is an image drawing to show a SET CONDITION YOURSELF screen in the auto observation mode in the scanning electron microscope operation program according to the embodiment of the invention.

The guide of the guidance function can also be stopped in the auto observation mode. If the operator presses a SET CONDITION YOURSELF button 812, a screen in FIG. 25 is displayed and enables the operator to enter all setup items entered according to the guidance function. Accordingly, the operator can specify any desired setup item regardless of the setting order presented by the guidance function. The SET CONDITION YOURSELF button 82 can be used, for example, when the operator who can grasp the operation procedure as a result of using the auto observation mode several times wants to set the image observation condition on one screen. Also in this case, an observation image can be provided as the operator enters only predetermined items without setting all image observation conditions manually; convenient use can be made.

Specifically, the operator uses a radio button to specify whether the specimen is conductor only or contains an insulator in a SPECIMEN CLASSIFICATION field 83. The operator uses a radio button to select any desired image observation condition from among various image observation conditions in an OBSERVATION CONDITION field 84. If the operator presses a SET TO ABOVE-SHOWN CONDITION button 85 after selecting the image observation condition, the detector, the acceleration voltage, and the spot size responsive to the image observation condition are automatically entered in corresponding condition fields. Each condition field is provided with a drop-down menu and the operator can also select any desired one out of displayed options. Further, if the operator presses an EXECUTE E-PREVIEW button 86, e-preview is started, the tab on the second display section 48 is switched to E-PREVIEW 51, and preview images in e-preview are drawn in order and are displayed. If the operator selects any desired preview image, the selected image is displayed on the first display section 47.

If the operator wants to use guidance-type observation condition setting according to the guidance function, the operator presses an AUTO CONDITION SETTING button 87. The screen returns to the screen in FIG. 6.

[Retain and Call Image Observation Condition]

The image observation condition can be retained and the retained image observation condition can be later read for use. The recommended image observation conditions of the acceleration voltage, the spot size, the magnification, etc., can also be preset in response to various specimens and observation purposes in the electron microscope or the computer, and can also be called. The operator can call appropriate setting in response to the situation and can change or adjust the setting as required for use.

Figure 26:
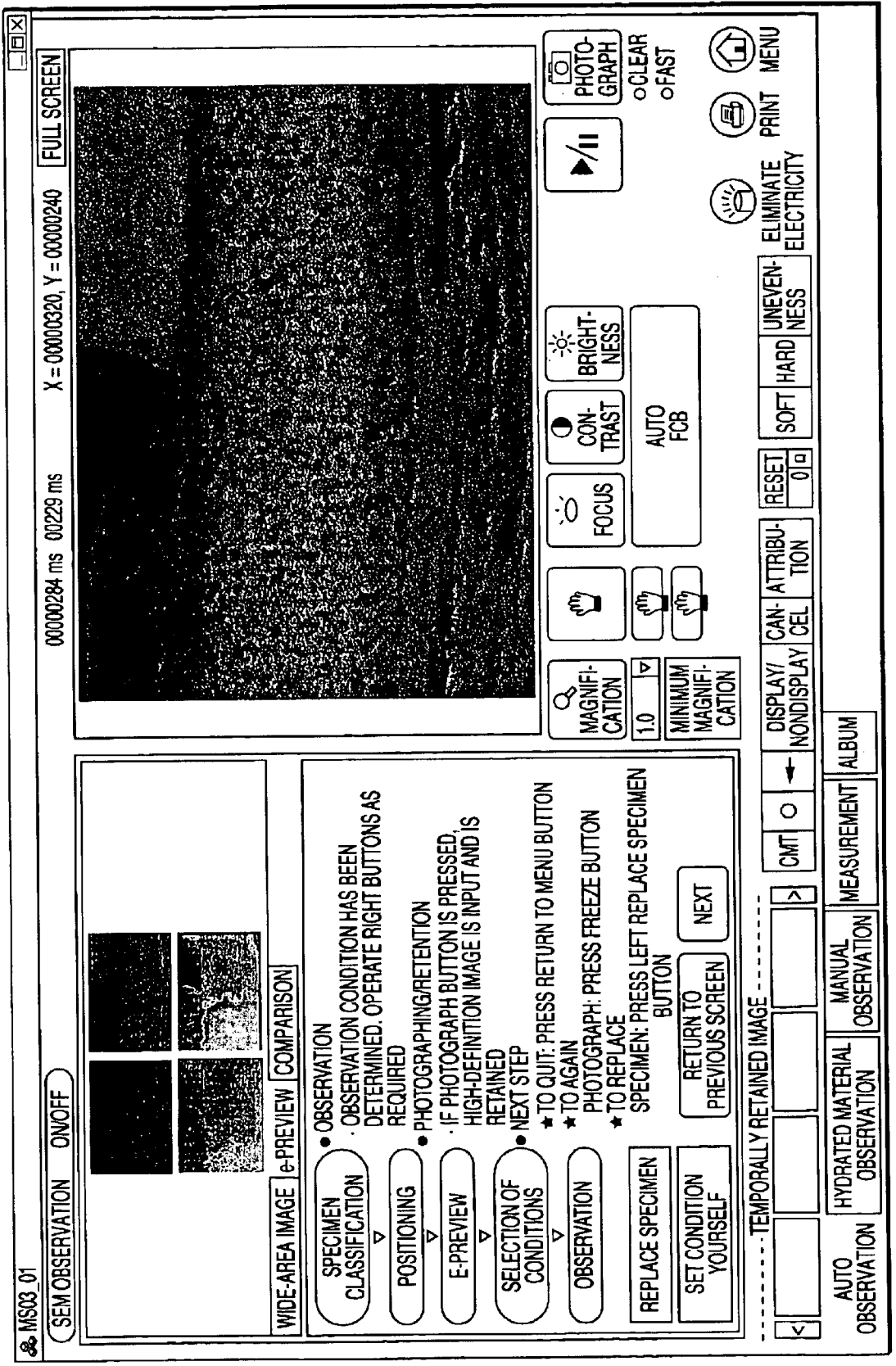
FIG. 26 is an image drawing to show an example of execution of e-preview in observing the glass epoxy board in FIGS. 20 to 23 in the auto observation mode in the scanning electron microscope operation program according to the embodiment of the invention.

In the example, a one-yen coin is used as the specimen and three secondary electron images and one reflection electron image are displayed as the preview images. In contrast, FIG. 26 shows an example of execution of e-preview in observing the glass epoxy board in FIGS. 20 to 23 as the specimen according to a similar procedure to that described above. In FIG. 26, secondary electron images are displayed as all preview images. Thus, as the preview images displayed in the second display section 48, secondary and reflection electron images are displayed in combination and in addition, only secondary electron images or only reflection electron images can also be displayed.

In the embodiment, the example of picking up four preview images by executing e-preview has been described, but the number of preview images to be picked up may be two or three or can also be five or more. How many preview images are to be displayed is determined in response to the time required for drawing each preview image, the image observation condition, etc.

As described above, according to the electron microscope, the electron microscope operation method, the electron microscope operation program, and the computer-readable record medium of the invention, even the operator who has poor experience in operating an electron microscope can set an image observation condition and acquire an observation image, because the electron microscope, the electron microscope operation method, the electron microscope operation program, and the computer-readable medium of the invention comprise the guidance function for guiding the operator in setting the image observation condition and automatically set the necessary items. Accordingly, minimum observation image can be acquired easily and it is made possible for the operator to further make necessary adjustment to generate any desired observation image. The ease-of-use of an electron microscope formerly difficult in setting and requiring a skill is improved and the electron microscope enables the operator to easily set image observation condition without special knowledge.

Thus, the operator is guided in setting by the guidance function and appropriate condition is computed, presented, etc., for supporting setting work, so that even the beginner unfamiliar with operating the electron microscope can acquire an observation image.

What is claimed is:

1. An electron microscope for picking up an observation image of a specimen based on an image observation condition, said electron microscope comprising:
   a first setting section for setting at least characteristics of the specimen as an image observation condition on a first image observation mode screen;
   a first display section for displaying an observation image of the specimen based on the condition set through said first setting section;
   a second display section for displaying at least one observation image of the specimen including at least one secondary electron image or at least one reflection electron image under at least two types of image observation conditions based on the condition set through said first setting section; and
   a selection section for selecting a desired observation image from among the observation images displayed on said second display section.

2. The electron microscope as claimed in claim 1, wherein the second display section displays a plurality of observation images of the specimen including a plurality of secondary electron images.

3. The electron microscope as claimed in claim 1, wherein the second display section displays a plurality o observation images of the specimen including a plurality of reflection electron images.

4. The electron microscope as claimed in claim 1, wherein the second display section displays a plurality of the observation images of the specimen including at least one secondary electron image and at least one reflection electron image.

5. The electron microscope as claimed in claim 1, further comprising:
   a second setting section for setting at least a spot size of an electron beam on the specimen, an acceleration voltage, a detector type, a specimen position, and an observation magnification as image observation conditions on a second image observation mode screen; and
   a mode switch section for switching said first image observation mode screen and said second image observation mode screen.

6. The electron microscope as claimed in claim 1, wherein the at least two types of image observation conditions include at least two types of acceleration voltages or spot sizes changed.

7. The electron microscope as claimed in claim 1, further comprising:
   an observation positioning section for moving the observation image displayed on said first display section to a predetermined position on said first display section; and
   an observation magnification change section for changing an observation magnification of the observation image displayed on said first display section,
   wherein said second display section displays the at least one observation images of the specimen at the observation position and the observation magnification set through the observation positioning section and the observation magnification change section.

8. The electron microscope as claimed in claim 1, further comprising:
an adjustment section for adjusting at least any of focus, contrast, or brightness with respect to the observation image selected through said selection section in the first image observation mode.

9. The electron microscope as claimed in claim 1, wherein the at least one secondary electron image includes a secondary electron image acquired with an acceleration voltage set to 5 kV or less and a secondary electron image acquired with an acceleration voltage set to 10 kV or more.

10. The electron microscope as claimed in claim 1, wherein the at least one reflection electron image includes a reflection electron image acquired with an acceleration voltage set to 10 kV or more.

11. The electron microscope as claimed in claim 1, wherein the acceleration voltage set for each of the secondary electron images or the reflection electron images displayed on said second display section is determined according to a predetermined procedure.

12. The electron microscope as claimed in claim 5, wherein the second setting section sets an astigmatism to a predetermined value on the second image observation mode screen.

13. The electron microscope as claimed in claim 5, wherein the second setting section sets an optical axis adjustment on the second image observation mode screen based on a correlation table prepared based on at least the relationship between the acceleration voltage and the spot size.

14. The electron microscope as claimed in claim 1, further comprising:
an automatic adjustment section for automatically adjusting an observation magnification of the observation image displayed on said first display section or said second display section to a magnification for enabling the whole of the specimen to be displayed.

15. An electron microscope comprising:
an electron gun for applying an electron beam;
a gun alignment coil for making a correction to the electron beam applied from said electron gun so that the electron beam passes through the center of a lens system;
a converging lens for narrowing down a size of a spot of the electron beam;
an electron beam deflection scanning coil for scanning the electron beam converged through said converging lens over a specimen;
a detector for detecting secondary electrons or reflection electrons output from the specimen with scanning;
a display section for displaying an observation image based on the secondary electrons or the reflection electrons; and
a guidance section for guiding an operator through a setting procedure of a setup item required for setting at least an acceleration voltage or spot size as an image observation condition.

16. The electron microscope as claimed in claim 15, wherein said guidance section prompts the operator to select or enter a setup item to be set in an interactive mode and determines a necessary setup item based on the setting by the operator.

17. The electron microscope as claimed in claim 15, wherein said guidance section comprises an explanation display section for explaining selection or entry of a setup item to be set and for displaying an explanation about the setup item to be set.

18. The electron microscope as claimed in claim 15, wherein said guidance section comprises:
a first setting section for selecting at least characteristics of the specimen as an image observation condition; and
an observation magnification change section for changing an observation magnification of an observation image of the specimen displayed on the display section based on the condition set through the first setting section.

19. The electron microscope as claimed in claim 18, wherein said display section comprises:
a first display section for displaying the observation image of the specimen based on the condition set through the first setting section; and
a second display section for displaying at least one observation image of the specimen including at least one secondary electron image or at least one reflection electron image under at least the acceleration voltage or the spot size changed at the observation magnification set through the observation magnification change section.

20. The electron microscope as claimed in claim 19, wherein said guidance section comprises:
an observation positioning section for moving the observation image displayed on the first display section to a predetermined position on the first display section.

21. A method for operating an electron microscope for picking up an observation image of a specimen based on an image observation condition, said method comprising:
setting at least characteristics of the specimen as an image observation condition on a first image observation mode screen;
displaying an observation image of the specimen on a first display section based on the condition set through said setting step;
displaying at least one observation image of the specimen including at least one secondary electron image or at least one reflection electron image under at least two types of image observation conditions based on the condition set through said setting step; and
selecting a desired observation image from among the observation images displayed on said second display section.

22. The electron microscope as claimed in claim 21, further comprising:
moving the observation image displayed on the first display section to a predetermined position on the first display section; and
determining an observation magnification of the observation image displayed on the first display section,
wherein the at least one observation image of the specimen is displayed on the second display section at the determined observation position and observation magnification.

23. The electron microscope as claimed in claim 21, further comprising:
moving the observation image displayed on the first display section to a predetermined position on the first display section; and adjusting the observation magnification of the observation image displayed on the first display section, wherein the at least one observation image of the specimen is displayed on the second display section at the adjusted observation magnification.

24. The electron microscope as claimed in claim 21, further comprising:

selecting either the first image observation mode screen or a second image observation mode screen as a screen for setting an image observation condition; and setting at least a spot size of an electron beam on the specimen, an acceleration voltage, a detector type, a specimen position, and an observation magnification when the second image observation mode screen is selected.

25. The electron microscope as claimed in claim 21, further comprising:

setting a predetermined setup item as a limitation item which is inhibited from being set in each step.

26. The electron microscope as claimed in claim 21, further comprising:

setting a predetermined setup item which need not be set as nondisplay setup item in each step.

27. The electron microscope as claimed in claim 23, wherein the observation image displayed on the first display section is automatically moves roughly to the center on the first display section based on a preset default value, and the observation magnification of the observation image displayed on the first display section is automatically adjusted based on a preset default value, and wherein the at least one observation image of the specimen is displayed on the second display section at the adjusted observation magnification.

* * * * *